(12) United States Patent
Shinohara et al.

(10) Patent No.: US 8,901,340 B2
(45) Date of Patent: Dec. 2, 2014

(54) COMPOUNDS CONTAINING PERFLUOROALKYL-CYANO-ALKOXY-BORATE ANIONS OR PERFLUOROALKYL-CYANO-ALKOXY-FLUORO-BORATE ANIONS

(75) Inventors: Hiromi Shinohara, Kanagawa (JP); Kentaro Kawata, Kanagawa (JP); Hiroki Yoshizaki, Mitaka (JP); Peer Kirsch, Seeheim-Jugenheim (DE); Nikolai (Mykola) Ignatyev, Duisburg (DE); William Robert Pitner, Corinth (MS); Michael Schulte, Bischofsheim (DE); Jan Sprener, Rommerskirchen (DE); Maik Finze, Nienburg (DE); Walter Frank, Wuppertal (DE)

(73) Assignee: Merck Patent GmbH, Darmstadt (DE)

( * ) Notice: Subject to any disclaimer, the term of this patent is extended or adjusted under 35 U.S.C. 154(b) by 218 days.

(21) Appl. No.: 13/522,598

(22) PCT Filed: Jan. 12, 2011

(86) PCT No.: PCT/EP2011/000091
§ 371 (c)(1),
(2), (4) Date: Jul. 17, 2012

(87) PCT Pub. No.: WO2011/085967
PCT Pub. Date: Jul. 21, 2011

(65) Prior Publication Data
US 2012/0296096 A1    Nov. 22, 2012

(30) Foreign Application Priority Data
Jan. 18, 2010    (EP) .................................... 10000407

(51) Int. Cl.
*C07F 5/02* (2006.01)
*H01G 9/20* (2006.01)
*H01M 14/00* (2006.01)
*H01L 51/00* (2006.01)

(52) U.S. Cl.
CPC . *C07F 5/02* (2013.01); *C07F 5/025* (2013.01); *H01L 51/0086* (2013.01); *Y02E 60/13* (2013.01); *Y02E 10/542* (2013.01); *H01G 9/2004* (2013.01); *H01M 14/005* (2013.01); *H01G 9/2031* (2013.01)
USPC .......................................... 558/384; 562/806

(58) Field of Classification Search
USPC .......................................... 558/384; 562/806
See application file for complete search history.

(56) References Cited

U.S. PATENT DOCUMENTS

| 6,815,119 | B2 | 11/2004 | Schmidt et al. |
| 6,861,722 | B2 | 3/2005 | Graetzel et al. |
| 7,208,626 | B2 | 4/2007 | Welz-Biermann et al. |
| 7,413,799 | B2 | 8/2008 | Hiruma et al. |
| 7,632,969 | B2 | 12/2009 | Welz-Biermann et al. |
| 7,700,781 | B2 | 4/2010 | Ignatyev et al. |
| 2005/0119513 | A1 | 6/2005 | Ignatyev et al. |
| 2007/0293391 | A1 | 12/2007 | Finze et al. |
| 2008/0214829 | A1 | 9/2008 | Ignatyev et al. |

FOREIGN PATENT DOCUMENTS

| EP | 0 986 079 | 3/2000 |
| EP | 1 180 774 | 2/2002 |
| EP | 1 205 480 | 5/2002 |
| EP | 1 507 307 | 2/2005 |
| JP | 2008 027766 | 2/2008 |
| WO | WO-91 16719 | 10/1991 |
| WO | WO-03 087020 | 10/2003 |
| WO | WO-03 087113 | 10/2003 |
| WO | WO-2006 010455 | 2/2006 |
| WO | 2006045405 | 5/2006 |
| WO | WO 2006/054505 | * 5/2006 ................. C08J 5/18 |
| WO | WO-2006 054505 | 5/2006 |
| WO | WO-2007 093961 | 8/2007 |
| WO | WO-2008 102661 | 8/2008 |
| WO | WO-2009 083901 | 7/2009 |

OTHER PUBLICATIONS

Adonin, N. Y. et al., "Polyfluoroorganoboron-Oxygen Compounds. 5 [1] Feasible Routes to Perfluoroalkyltrimethoxyborates $M[C_nF_{2n+1}B(OMe)_3]$ (n≥3)," Organometallics, 2007, vol. 26, pp. 2420-2425.

Barbé, C. J. et al., "Nanocrystalline titanium oxide electrodes for photovoltaic Applications," J. Am. Chem. Soc., 1997, vol. 80, No. 12, pp. 3157-3171.

Bernhardt, E. et al., "An efficient synthesis for tetracyanoborates by sinter processes," Z. Anotg. Allg. Chem., 2003, vol. 629, pp. 1229-1234.

Bernhardt, E. et al., "Die Reaktionen von $M[BF_4]$ (M=Li, K) und $(C_2H_5)_2O$ $BF_3$ mit $(CH_3)_3SiCN$. Bildung von $M[BF_x(CN)_{4-x}]$ (M = Li, K; x = 1,2) und $(CH_3)3SiNCBF_x(CN)_{3-x1}$ (x=0,1).," Z. Anorg. Allg. Chem., 2003, vol. 627, pp. 677-685.

Bernhardt, E. et al., "Synthesis and properties of the Tetrakis (trifluoromethyl)borate Anion, $[B(CF_3)_4]$-: Structure determination of $Cs[B(CF_3)_4]$ by Single-Crystal X-ray Diffraction," Chem. Eur. J., 2001, vol. 7, No. 21, pp. 4696-4704.

(Continued)

*Primary Examiner* — Joseph Kosack
(74) *Attorney, Agent, or Firm* — Millen, White, Zelano & Branigan, P.C.

(57) ABSTRACT

The present invention relates to compounds containing perfluoroalkyl-cyano-alkoxy-borate anions or perfluoroalkyl-cyano-alkoxy-fluoro-borate anions, ((per)fluoro)phenyl-cyano-alkoxy-borate anions or ((per)fluoro)phenyl-cyano-alkoxy-fluoro-borate anions or phenyl-cyano-alkoxy-borate anions which are monosubstituted or disubstituted with perfluoroalkyl groups having 1 to 4 C atoms or phenyl-cyano-alkoxy-fluoro-borate anions which are monosubstituted or disubstituted with perfluoroalkyl groups having 1 to 4 C atoms, the preparation thereof and the use thereof, in particular as part of electrolyte formulations for dye sensitized solar cells.

15 Claims, 2 Drawing Sheets

(56) References Cited

OTHER PUBLICATIONS

Bernhardt, E. et al., "The tetracyanoborates M[B(CN)$_4$], M=[Bu$_4$N]$^+$, Ag$^+$, K$^+$," Z. Anorg. Allg. Chem., 2000, vol. 626, pp. 560-568.

Chambers, R. D. et al., "Some Salts of trifluoromethylfluoroboric Acid 1,2," Contribution from the Chemistry Department, University of British Columbia, Mar. 29, 1960, vol. 82, pp. 5298-5301.

Earle, M. J. et al., "Ionic Liquids. Green solvents for the future," Pure Appl. Chem., 2000, vol. 72, No. 7, pp. 1391-1398.

Frohn, H. J. et al., "A preparative method for perfluoroalkyltrifluoroborates and Perfluoroalkyldifluoroboranes," Z. Anorg. Allg. Chem., 2001, vol. 627, pp. 15-16.

Hagiwara, R. et al., "Room temperature ionic liquids of alkylimidazolium cations and fluoroanions," Journal of Fluorine Chemistry, 2000, vol. 105, pp. 221-227.

International Search Report for PCT/EP2011/000091 dated Mar. 8, 2011.

Kolomeitsev, A. A. et al., "Perfluoroalkyl borates and boronic esters: new promising partners for Suzuki and Petasis reactions," Tetrahedron Letters, 2003, vol. 44, pp. 8273-8277.

Molan Der, G. A. et al., "Improved synthesis of Potassium (Trifluoromethyl)trifluoroborate [K(CF$_3$BF$_3$)]," Organometallics, 2003, vol. 22, pp. 3313-3315.

Rasmussen, J. K. et al., "The Chemistry of Cyanotrimethylsilane," Advances in Silicon Chemistry, 1991, vol. 1, pp. 65-187.

Sheldon, R., "Catalytic reactions in ionic liquids," Chem. Commun., 2001, pp. 2399-2407.

Wang, P. et al., "Enhance the performance of dye-sensitized solar cells by co-grafting amphiphillic sensitizer and hexadecylmalonic Acid on TiO$_2$ Nanocrystals," J. Phys. Chem. B, 2003, vol. 107, pp. 14336-14341.

Wasserscheid, P. et al., Angew. Chem., 2000, vol. 112, pp. 3926-3945.

Welton, T. et al., "Room-temperature ionic liquids. Solvents for Synthesis and Catalysis," Chem. Rev., 1999, vol. 99, pp. 2071-2083.

Zhou, Z. et al., "Novel electrolyte salts based on perfluoroalkyltrifluoroborate anions 1. Synthesis and characterization," Journal of Fluorine Chemistry, 2003, vol. 123, pp. 127-131.

Hitachi Maxell Ltd., "Lithium Battery," Patent Abstracts of Japan, Publication Date: Feb. 7, 2008; English Abstract of JP-2008 027766.

Toyo Kasei Kogyo Co Ltd., "Method for producing trialkylsilylnitrile," Espacenet, Publication Date: Aug. 28, 2008; English Abstract of WO-2008 102661.

Adonin, N. Y. et al., "Polyfluoroorganoboron-Oxygen Compounds. 5 [1] Feasible Routes to Perfluoroalkyltrimethoxyborates M[C$_n$F$_{2n+1}$B(OMe)3] (n≥3)," Z. Amorg. Allg. Chem., 633:647-652 (2007).

Adonin, N. Y. et al., "(Fluoroorgano)fluoroboranes and -borates. 16. Preparation of Bis(perfluoroalkyl) dimethoxyborate and Bis(perfluoroalkyl)difluoroborate Salts, M[C$_n$F$_{2n+1}$)$_2$BX$_2$] (M = K, NMe4; X=OMe,F)", Organometallics, 26:2420-2425 (2007).

Reetz, M.T. et al., "An Improved Synthesis of Cyanotrimethylsilane", Synthesis, 330 (1982).

* cited by examiner

COMPOUNDS CONTAINING PERFLUOROALKYL-CYANO-ALKOXY-BORATE ANIONS OR PERFLUOROALKYL-CYANO-ALKOXY-FLUORO-BORATE ANIONS

The present invention relates to compounds containing perfluoroalkyl-cyano-alkoxy-borate anions or perfluoroalkyl-cyano-alkoxy-fluoro-borate anions, ((per)fluoro)phenyl-cyano-alkoxy-borate anions or ((per)fluoro)phenyl-cyano-alkoxy-fluoro-borate anions or phenyl-cyano-alkoxy-borate anions which are monosubstituted or disubstituted with perfluoroalkyl groups having 1 to 4 C atoms or phenyl-cyano-alkoxy-fluoro-borate anions which are monosubstituted or disubstituted with perfluoroalkyl groups having 1 to 4 C atoms, the preparation thereof and the use thereof, in particular as part of electrolyte formulations for dye sensitized solar cells.

The salts according to the invention can on the one hand be used for the synthesis of ionic liquids, on the other hand the salts can be employed per se as ionic liquid.

Ionic liquids or liquid salts are ionic species which consist of an organic cation and a generally inorganic anion. They do not contain any neutral molecules and usually have melting points below 373 K.

The area of ionic liquids is currently the subject of intensive research since the potential applications are multifarious. Review articles on ionic liquids are, for example, R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionische Flüssigkeiten—neue Lösungen für die Übergangsmetallkatalyse" [Ionic Liquids—Novel Solutions for Transition-Metal Catalysis], *Angew. Chem.*, 112 (2000), 3926-3945; T. Welton "Room temperature ionic liquids. Solvents for synthesis and catalysis", *Chem. Rev.*, 92 (1999), 2071-2083 or R. Hagiwara, Ya. Ito "Room temperature ionic liquids of alkylimidazolium cations and fluoroanions", *J. Fluorine Chem.*, 105 (2000), 221-227.

The properties of ionic liquids, for example melting point, thermal and electrochemical stability, viscosity, are strongly influenced by the nature of the anion.

E. Bernhardt et al, Z. Anorg. Allg. Chem. 2000, 626, 560, E. Bernhardt et al, Chem. Eur. J. 2001, 7, 4696 and E. Bernhardt et al, Z. Anorg. Allg. Chem. 2003, 629, 1229 disclose the novel chemically and electrochemically stable borate anions $[B(CN)_4]^-$, $[F_xB(CN)_{4-x}]^-$, where x=1 to 3, and $[B(CF_3)_4]^-$.

EP 1205480 A1 describes tetrakisfluoroalkylborate salts and the use thereof as conductive salts or ionic liquids.

WO 2006/010455 describes alkoxytris(perfluoroalkyl)borate salts and their use as precursor for the synthesis of ionic liquids or their use as ionic liquids.

WO 2006/045405 describes salts of the formula $[B(R_f)_{4-x-y}(CN)_x(F)_y]^-$ in which x is 1, 2 or 3, y=0 or 1, x+y≤4 and $R_f$ denotes a perfluorinated or partially fluorinated alkyl group having 1 to 12 C atoms, particularly potassium tris(trifluoromethyl)cyanoborate, guanidinium tris(trifluoromethyl)cyanoborate and tritylium tris(trifluoromethyl)cyanoborate.

The object of the present invention was to provide alternative compounds which are novel, thermally and electrochemically stable which can be used for the synthesis of ionic liquids or as ionic liquids, and which are in particular useful for the synthesis of ionic liquids or as ionic liquids for application in dye sensitized solar cells.

The object is achieved by the salts of the formula I according to the invention with the specific borate anions of formula Ia.

The invention therefore relates to compounds containing borate anions of formula Ia

$$[B(R_f)(CN)_x(OR^*)_{3-x-y}(F)_y]^{-1} \qquad \text{Ia}$$

in which x is 1 or 2, y is 0 or 1 and x+y is <3,
$R_f$ denotes straight-chain or branched perfluoroalkyl groups having 1 to 4 C atoms, $C_6F_5$, $C_6H_5$, partially fluorinated phenyl or phenyl which is monosubstituted or disubstituted by perfluoroalkyl groups having 1 to 4 C atoms and
R* denotes straight-chain or branched alkyl groups having 1 to 4 C atoms.

The invention relates in addition to compounds of formula I

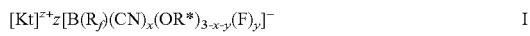

$$[Kt]^{z+}z[B(R_f)(CN)_x(OR^*)_{3-x-y}(F)_y]^- \qquad \text{I}$$

in which $[Kt]^{z+}$ denotes an inorganic or organic cation or $H^+$,
z is 1 or 2
x is 1 or 2, y is 0 or 1 and x+y is <3,
$R_f$ denotes straight-chain or branched perfluoroalkyl groups having 1 to 4 C atoms, $C_6F_5$, $C_6H_5$, partially fluorinated phenyl or phenyl which is monosubstituted or disubstituted by perfluoroalkyl groups having 1 to 4 C atoms and
R* denotes straight-chain or branched alkyl groups having 1 to 4 C atoms.

A straight-chain or branched perfluoroalkyl group having 1 to 4 C atoms is, for example, trifluoromethyl, pentafluoroethyl, heptafluoropropyl, heptafluoroisopropyl, nonafluorobutyl, nonafluoro-sec.-butyl or nonafluoro-tert.-butyl.

A straight-chain or branched alkyl group having 1 to 4 C atoms is, for example, methyl, ethyl, propyl, isopropyl, n-butyl, sec.-butyl or tert.-butyl.

$R_f$ in formula Ia or in formula I is in particular trifluoromethyl, pentafluoroethyl or heptafluoropropyl, $C_6F_5$, p-$FC_6H_4$, 3,5-$(CF_3)_2C_6H_3$ or $C_6H_5$, particularly preferably straight-chain or branched perfluoroalkyl groups having 1 to 4 C atoms or $C_6F_5$, very particularly preferably trifluoromethyl or pentafluoroethyl.

R* in formula Ia or in formula I is in particular methyl, ethyl, n-propyl or n-butyl, particularly preferably methyl or ethyl, especially particularly preferably methyl.

There are no restrictions per se regarding the choice of cation of the compound of formula I in accordance with the present invention. Thus, $[Kt]^{z+}$ can be an inorganic or organic cation. Compounds of formula I with alkalimetal cations are preferred starting materials for the synthesis of compounds of formula I having organic cations or metal cations other than alkalimetal cations. The cations are preferably organic cations when the use of salts of formula I is in the field of applications for ionic liquids. The cations are preferably metal cations when the use of the salts of formula I is as precursors for the synthesis of ionic liquids, conducting salts with organic cations or Brønsted acids or in the field of catalysis, conductive salts for electrochemical devices or sensors.

Preferably the organic cations are selected from the group comprising sulfonium, oxonium, ammonium, phosphonium, uronium, thiouronium, guanidinium cations or heterocyclic cations. Examples of organic cations are also polyammonium ions having a degree of charging z=4 or tritylium cation in which the phenyl groups may be substituted by straight-chain or branched alkyl groups having 1 to 20 C atoms, straight-chain or branched alkenyl having 2 to 20 C atoms and one or more double bonds or straight-chain or branched alkynyl having 2 to 20 C atoms and one or more triple bonds.

Sulfonium cations can be described, for example by the formula (1) and oxonium cations can be described, for example, by the formula (2)

  (1)

  (2), where $R^o$ denotes straight-chain or branched alkyl groups having 1-8 C atoms, $R'''_2N$— or nonsubstituted phenyl or phenyl which is substituted by $R'''$, $OR'''$, $N(R''')_2$, CN or halogen and $R'''$ is independently of each other H or straight-chain or branched $C_1$ to $C_8$ alkyl.

$R^o$ of the $[(R^o)_3O]^+$ cation or $[(R^o)_3S]^+$ cation is preferably straight-chain alkyl having 1-8 C atoms or nonsubstituted phenyl or phenyl which is substituted by $R'''$, $OR'''$, $N(R''')_2$, CN or halogen and $R'''$ is independently of each other H or straight-chain or branched $C_1$ to $C_8$ alkyl, particularly preferably straight-chain alkyl having 1-8 C atoms, in particular methyl or ethyl, very particularly preferably ethyl. A particularly preferred sulfonium cation is diethyl-methylsulfonium.

Ammonium cations can be described, for example, by the formula (3)

  (3), where
R in each case, independently of one another, denotes
H,
OR', NR'$_2$, with the proviso that a maximum of one substituent R in formula (3) is OR', NR'$_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms,
which may be substituted by alkyl groups having 1-6 C atoms, where one or two R may be partially or fully substituted by halogens, in particular —F and/or —Cl, or partially by —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', —NO$_2$ and where one or two non-adjacent carbon atoms in R which are not in the α-position may be replaced by atoms and/or atom groups selected from the group —O—, —S—, —S(O)—, —SO$_2$—, —SO$_2$O—, —C(O)—, —C(O)O—, —N'R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R' may be =H, non-, partially or perfluorinated $C_1$- to $C_{18}$-alkyl, $C_3$- to $C_7$-cycloalkyl, nonsubstituted or substituted phenyl and X may be =halogen.

Phosphonium cations can be described, for example, by the formula (4)

  (4), where
$R^2$ in each case, independently of one another, denotes
H, OR' or NR'$_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms,
which may be substituted by alkyl groups having 1-6 C atoms, where one or two $R^2$ may be partially or fully substituted by halogens, in particular —F and/or —Cl, or partially by —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', —NO$_2$ and where one or two non-adjacent carbon atoms in $R^2$ which are not in the α-position may be replaced by atoms and/or atom groups selected from the group —O—, —S—, —S(O)—, —SO$_2$—, —SO$_2$O—, —C(O)—, —C(O)O—, —N'R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=H, non-, partially or perfluorinated $C_1$- to $C_{18}$-alkyl, $C_3$- to $C_7$-cycloalkyl, nonsubstituted or substituted phenyl and X=halogen.

However, cations of the formulae (3) and (4) in which all four or three substituents R and $R^2$ are fully substituted by halogens are excluded, for example the tris(trifluoromethyl)methylammonium cation, the tetrakis(tri-fluoromethyl)ammonium cation or the tetrakis(nonafluorobutyl)ammonium cation.

Uronium cations can be described, for example, by the formula (5)

  (5), and thiouronium cations by the formula (6)

  (6), where
$R^3$ to $R^7$ each, independently of one another, denote
H, where H is excluded for $R^5$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms, where one or more of the substituents $R^3$ to $R^7$ may be partially or fully substituted by halogens, in particular —F and/or —Cl, or partially by —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', —NO$_2$ and where one or two non-adjacent carbon atoms in $R^3$ to $R^7$ which are not in the α-position may be replaced by atoms and/or atom groups selected from the group —O—, —S—, —S(O)—, —SO$_2$—, —SO$_2$O—, —C(O)—, —C(O)O—, —N'R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=H, non-, partially or perfluorinated $C_1$- to $C_{18}$-alkyl, $C_3$- to $C_7$-cycloalkyl, nonsubstituted or substituted phenyl and X=halogen.

Guanidinium cations can be described by the formula (7)

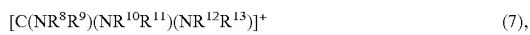  (7), where
$R^8$ to $R^{13}$ each, independently of one another, denote
H, —CN, NR'$_2$, —OR',
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms, where one or more of the substituents $R^8$ to $R^{13}$ may be partially or fully substituted by halogens, in particular —F and/or —Cl, or partially by —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', —NO$_2$ and where one or two non-adjacent carbon atoms in $R^8$ to $R^{13}$ which are not in the α-position may be replaced by atoms and/or atom groups selected from the group —O—, —S—, —S(O)—, —SO$_2$—, —SO$_2$O—, —C(O)—, —C(O)O—, —N'R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=H, non-, partially or perfluorinated $C_1$- to $C_{18}$-alkyl, $C_3$- to $C_7$-cycloalkyl, nonsubstituted or substituted phenyl and X=halogen.

Heterocyclic cations can be described, for example by the formula (8)

$$[HetN]^{z+} \tag{8}$$

where

HetN$^{z+}$ denotes a heterocyclic cation selected from the group imidazolium 1H-pyrazolium 3H-pyrazolium 4H-pyrazolium 1-pyrazolinium 2-pyrazolinium 3-pyrazolinium 2,3-dihydroimidazolinium 4,5-dihydroimidazolinium 2,5-dihydroimidazolinium pyrrolidinium 1,2,4-triazolium 1,2,4-triazolium 1,2,3-triazolium 1,2,3-triazolium pyridinium pyridazinium pyrimidinium piperidinium morpholinium piperazinium piperazinium pyrazinium thiazolium oxazolium -continued

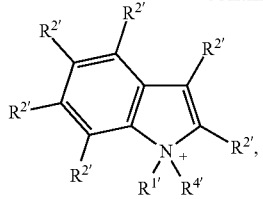
indolium

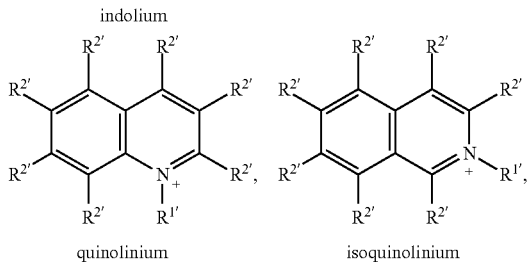
quinolinium    isoquinolinium

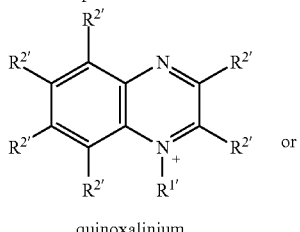
quinoxalinium

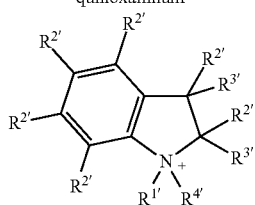
indolinium where the substituents
$R^{1'}$ to $R^{4'}$ each, independently of one another, denote
H,
F, Cl, Br, I, —CN, —OR', —NR'$_2$, —P(O)R'$_2$, —P(O)(OR')$_2$, —P(O)(NR'$_2$)$_2$, —C(O)R', —C(O)OR', —C(O)X, —C(O)NR'$_2$, —SO$_2$NR'$_2$, —SO$_2$OH, —SO$_2$X, —SR', —S(O)R', —SO$_2$R' and/or NO$_2$, with the proviso that $R^{1'}$, $R^{3'}$, $R^{4'}$ are H and/or a straight-chain or branched alkyl having 1-20 C atoms, straight-chain or branched alkenyl having 2-20 C atoms and one or more double bonds,
straight-chain or branched alkyl having 1-20 C atoms, which optionally may be fluorinated or perfluorinated,
straight-chain or branched alkenyl having 2-20 C atoms and one or more double bonds, which optionally may be fluorinated or perfluorinated,
straight-chain or branched alkynyl having 2-20 C atoms and one or more triple bonds, which optionally may be fluorinated or perfluorinated
saturated, partially or fully unsaturated cycloalkyl having 3-7 C atoms, which may be substituted by alkyl groups having 1-6 C atoms,
saturated, partially or fully unsaturated heteroaryl, heteroaryl-C$_1$-C$_6$-alkyl or aryl-C$_1$-C$_6$-alkyl,
where the substituents $R^{1'}$, $R^{2'}$, $R^{3'}$ and/or $R^{4'}$ together may also form a ring system,
where one or more substituents $R^{1'}$ to $R^{4'}$ may be partially or fully substituted by halogens, in particular —F and/or —Cl, or —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', —NO$_2$, but where $R^{1'}$ and $R^{4'}$ cannot simultaneously be fully substituted by halogens and where, in the substituents $R^{1'}$ to $R^{4'}$, one or two non-adjacent carbon atoms which are not bonded to the heteroatom may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=H, non-, partially or perfluorinated C— to C$_{18}$-alkyl, C$_3$- to C$_7$-cycloalkyl, non-substituted or substituted phenyl and X=halogen.

For the purposes of the present invention, fully unsaturated substituents are also taken to mean aromatic substituents.

In accordance with the invention, suitable substituents R and $R^2$ to $R^{13}$ of the compounds of the formulae (3) to (7), besides H, are preferably: $C_1$- to $C_{20}$-, in particular $C_1$- to $C_{14}$-alkyl groups, and saturated or unsaturated, i.e. also aromatic, $C_3$- to $C_7$-cycloalkyl groups, which may be substituted by $C_1$- to $C_6$-alkyl groups, in particular phenyl.

The substituents R and $R^2$ in the compounds of the formula (3) or (4) may be identical or different. The substituents R and $R^2$ are preferably different.

The substituents R and $R^2$ are particularly preferably methyl, ethyl, iso-propyl, propyl, butyl, sec-butyl, pentyl, hexyl, octyl, decyl or tetradecyl.

Up to four substituents of the guanidinium cation $[C(NR^8R^9)(NR^{10}R^{11})(NR^{12}R^{13})]^+$ may also be bonded in pairs in such a way that mono-, bi- or polycyclic cations are formed.

Without restricting generality, examples of such guanidinium cations are:

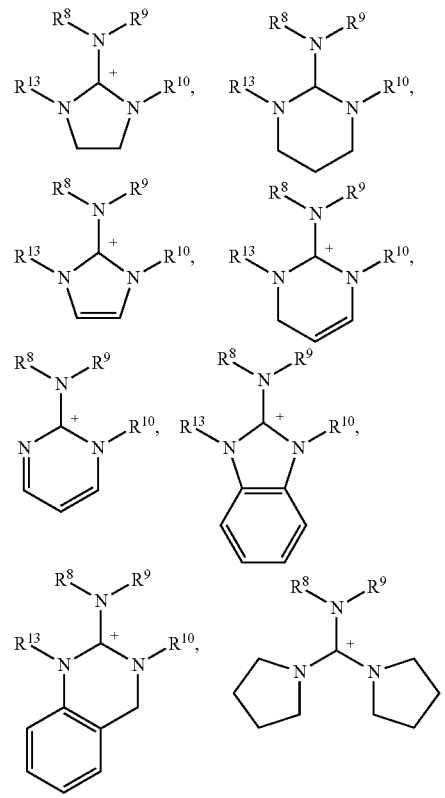

-continued

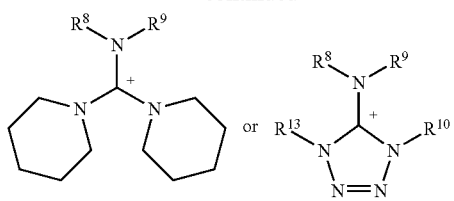

where the substituents $R^8$ to $R^{10}$ and $R^{13}$ can have a meaning or particularly preferred meaning indicated above.

If desired, the carbocycles or heterocycles of the guanidinium cations indicated above may also be substituted by $C_1$- to $C_6$-alkyl, $C_1$- to $C_6$-alkenyl, —CN, —NO$_2$, F, Cl, Br, I, —OH, —$C_1$-$C_6$-alkoxy, —NR'$_2$, —SR', —S(O)R', —SO$_2$R', —COOH, —SO$_2$NR'$_2$, —SO$_2$X' or —SO$_3$H, where X and R' have a meaning indicated above, substituted or nonsubstituted phenyl or an nonsubstituted or substituted heterocycle.

Up to four substituents of the uronium cation [C(NR$^3$R$^4$)(OR$^5$)(NR$^6$R$^7$)]$^+$ or thiouronium cation [C(NR$^3$R$^4$)(SR$^5$)(NR$^6$R$^7$)]$^+$ may also be bonded in pairs in such a way that mono-, bi- or polycyclic cations are formed.

Without restricting generality, examples of such cations are indicated below, where Y=O or S:

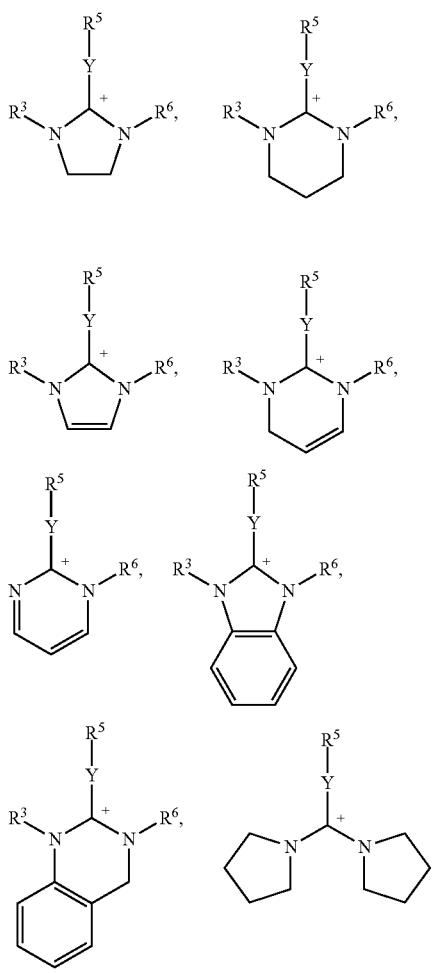

-continued

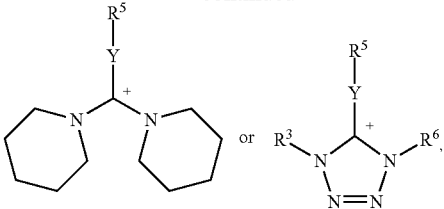

where the substituents $R^3$, $R^5$ and $R^6$ can have a meaning or particularly preferred meaning indicated above.

If desired, the carbocycles or heterocycles of the cations indicated above may also be substituted by $C_1$- to $C_6$-alkyl, $C_1$- to $C_6$-alkenyl, —CN, —NO$_2$, F, Cl, Br, I, —OH, —$C_1$-$C_6$-alkoxy, —NR'$_2$, —SR', —S(O)R', —SO$_2$R', —COOH, SO$_2$NR'$_2$, SO$_2$X or SO$_3$H or substituted or nonsubstituted phenyl or an nonsubstituted or substituted heterocycle, where X and R' have a meaning indicated above.

The substituents $R^3$ to $R^{13}$ are each, independently of one another, preferably a straight-chain or branched alkyl group having 1 to 16 C atoms. The substituents $R^3$ and $R^4$, $R^6$ and $R^7$, $R^8$ and $R^9$, $R^{10}$ and $R^{11}$ and $R^{12}$ and $R^{13}$ in compounds of the formulae (5) to (7) may be identical or different. $R^3$ to $R^{13}$ are particularly preferably each, independently of one another, methyl, ethyl, n-propyl, isopropyl, n-butyl, tert-butyl, sec-butyl, phenyl, hexyl or cyclohexyl, very particularly preferably methyl, ethyl, n-propyl, isopropyl, n-butyl or hexyl.

In accordance with the invention, suitable substituents $R^{1'}$ to $R^{4'}$ of compounds of the formula (8) are each, independently of one another, preferably, H with the assumption that $R^{1'}$ and $R^{4'}$ are not simultaneously H, straight-chain or branched alkyl having 1 to 20 C atoms, which optionally may be fluorinated or perfluorinated, straight-chain or branched alkenyl having 2 to 20 C atoms and one or more double bonds, which optionally may be fluorinated or perfluorinated, straight-chain or branched alkynyl having 2 to 20 C atoms and one or more triple bonds which optionally may be fluorinated or perfluorinated or straight-chain or branched alkoxyalkyl having 2 to 8 C atoms.

In accordance with the invention, suitable substituents $R^{1'}$ to $R^{4'}$ of compounds of formula (8) besides H with the assumption that $R^{1'}$ and $R^{4'}$ are not simultaneously H, are particularly preferably: C— to $C_{20}$—, in particular $C_1$- to $C_{12}$-alkyl groups, and saturated or unsaturated, i.e. also aromatic, $C_3$- to $C_7$-cycloalkyl groups, which may be substituted by $C_1$- to $C_6$-alkyl groups, in particular phenyl.

The substituents $R^{1'}$ and $R^{4'}$ are each, independently of one another, particularly preferably methyl, ethyl, allyl, isopropyl, propyl, butyl, sec-butyl, tert-butyl, pentyl, hexyl, octyl, decyl, cyclohexyl, phenyl or benzyl. They are very particularly preferably methyl, ethyl, n-butyl or hexyl. In pyrrolidinium, piperidinium or indolinium compounds, the two substituents $R^{1'}$ and $R^{4'}$ are preferably different.

The substituent $R^{2'}$ or $R^{3'}$ is in each case, independently of one another, in particular H, methyl, ethyl, isopropyl, propyl, butyl, sec-butyl, tert-butyl, cyclohexyl, phenyl or benzyl. $R^{2'}$ is particularly preferably H, methyl, ethyl, isopropyl, propyl, butyl or sec-butyl. $R^{2'}$ and $R^{3'}$ are very particularly preferably H.

The $C_1$-$C_{12}$-alkyl group is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl, hexyl, heptyl, octyl, nonyl, decyl, undecyl or dodecyl, which optionally may be fluorinated or perfluorinated. The term "perfluorinated" means that all H atoms are substituted by F atoms in the given alkyl group. The term "fluorinated" means that at least one H atom of the given alkyl group is substituted by an F atom such as difluoromethyl, trifluoromethyl, pentafluoroethyl, heptafluoropropyl or nonafluorobutyl.

A straight-chain or branched alkenyl having 2 to 20 C atoms, in which a plurality of double bonds may also be present, is, for example, allyl, 2- or 3-butenyl, isobutenyl, sec-butenyl, furthermore 4-pentenyl, isopentenyl, hexenyl, heptenyl, octenyl, $-C_9H_{17}$, $-C_{10}H_{19}$ to $-C_{20}H_{39}$, preferably allyl, 2- or 3-butenyl, isobutenyl, sec-butenyl, furthermore preferably 4-pentenyl, iso-pentenyl or hexenyl, which optionally may be fluorinated or perfluorinated. The term "perfluorinated" means that all H atoms are substituted by F atoms in the given alkyl group. The term "fluorinated" means that at least one H atom of the given alkyl group is substituted by an F atom.

A straight-chain or branched alkynyl having 2 to 20 C atoms, in which a plurality of triple bonds may also be present, is, for example, ethynyl, 1- or 2-propynyl, 2- or 3-butynyl, furthermore 4-pentynyl, 3-pentynyl, hexynyl, heptynyl, octynyl, $-C_9H_{15}$, $-C_{10}H_{17}$ to $-C_{20}H_{37}$, preferably ethynyl, 1- or 2-propynyl, 2- or 3-butynyl, 4-pentynyl, 3-pentynyl or hexynyl, which optionally may be fluorinated or perfluorinated. The term "perfluorinated" mean that all H atoms are substituted by F atoms in the given alkyl group. The term "fluorinated" mean that at least one H atom of the given alkyl group is substituted by an F atom.

A straight-chain or branched alkoxyalkyl having 2 to 12 C atoms is, for example, methoxymethyl, 1-methoxyethyl, 1-methoxypropyl, 1-methoxy-2-methyl-ethyl, 2-methoxypropyl, 2-methoxy-2-methyl-propyl, 1-methoxybutyl, 1-methoxy-2,2-dimethyl-ethyl, 1-methoxy-pentyl, 1-methoxyhexyl, 1-methoxy-heptyl, ethoxymethyl, 1-ethoxyethyl, 1-ethoxypropyl, 1-ethoxy-2-methyl-ethyl, 1-ethoxybutyl, 1-ethoxy-2,2-dimethyl-ethyl, 1-ethoxypentyl, 1-ethoxyhexyl, 1-methoxyheptyl, propoxymethyl, 1-propoxyethyl, 1-propoxypropyl, 1-propoxy-2-methyl-ethyl, 1-propoxybutyl, 1-propoxy-2,2-dimethyl-ethyl, 1-propoxypentyl, butoxymethyl, 1-butoxyethyl, 1-butoxypropyl or 1-butoxybutyl. Particularly preferred is methoxymethyl, 1-methoxyethyl, 2-methoxy-propyl, 1-methoxypropyl, 2-methoxy-2-methyl-propyl or 1-methoxybutyl.

Aryl-$C_1$-$C_6$-alkyl denotes, for example, benzyl, phenylethyl, phenylpropyl, phenylbutyl, phenylpentyl or phenylhexyl, where both the phenyl ring and also the alkylene chain may be partially or fully substituted, as described above, by halogens, in particular —F and/or —Cl, or partially by —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', —NO$_2$.

Nonsubstituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, each of which may be substituted by $C_1$- to $C_6$-alkyl groups, where the cycloalkyl group or the cycloalkyl group substituted by $C_1$- to $C_6$-alkyl groups may in turn also be substituted by halogen atoms, such as F, Cl, Br or I, in particular F or Cl, or by —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', —NO$_2$.

In the substituents R, $R^2$ to $R^{13}$ or $R^{1'}$ to $R^{4'}$, one or two non-adjacent carbon atoms which are not bonded in the α-position to the heteroatom may also be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'—, where R'=non-, partially or perfluorinated $C_1$- to $C_{18}$-alkyl, $C_3$- to $C_7$-cycloalkyl, nonsubstituted or substituted phenyl.

Without restricting generality, examples of substituents R, $R^2$ to $R^{13}$ and $R^{1'}$ to $R^{4'}$ modified in this way are: —OCH$_3$, —OCH(CH$_3$)$_2$, —CH$_2$OCH$_3$, —CH$_2$—CH$_2$—O—CH$_3$, —C$_2$H$_4$OCH(CH$_3$)$_2$, —C$_2$H$_4$C$_2$H$_5$, —C$_2$H$_4$SCH(CH$_3$)$_2$, —S(O)CH$_3$, —SO$_2$CH$_3$, —SO$_2$C$_6$H$_5$, —SO$_2$C$_3$H$_7$, —SO$_2$CH(CH$_3$)$_2$, —SO$_2$CH$_2$CF$_3$, —CH$_2$SO$_2$CH$_3$, —O—C$_4$H$_8$—O—C$_4$H$_9$, —CF$_3$, —O$_2$F$_5$, —C$_3$F$_7$, —C$_4$F$_9$, —C(CF$_3$)$_3$, —CF$_2$SO$_2$CF$_3$, —C$_2$F$_4$N(C$_2$F$_5$)C$_2$F$_5$, —CHF$_2$, —CH$_2$CF$_3$, —C$_2$F$_2$H$_3$, —C$_3$FH$_6$, —CH$_2$C$_3$F$_7$, —C(CFH$_2$)$_3$, —CH$_2$C(O)OH, —CH$_2$C$_6$H$_5$, —C(O)C$_6$H$_5$ or P(O)(C$_2$H$_5$)$_2$.

In R', $C_3$- to $C_7$-cycloalkyl is, for example, cyclopropyl, cyclobutyl, cyclopentyl, cyclohexyl or cycloheptyl.

In R', substituted phenyl denotes phenyl which is substituted by C— to $C_6$-alkyl, $C_1$- to $C_6$-alkenyl, —CN, —NO$_2$, F, Cl, Br, I, —OH, —C$_1$-C$_6$-alkoxy, NR'$_2$, —COOH, —SO$_2$X', —SR", —S(O)R", —SO$_2$R", SO$_2$NR'$_2$ or SO$_3$H, where X' denotes F, Cl or Br and R" denotes a non-, partially or perfluorinated C— to $C_6$-alkyl or $C_3$- to $C_7$-cycloalkyl as defined for R', for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-nitrophenyl, o-, m- or p-hydroxyphenyl, o-, m- or p-methoxyphenyl, o-, m- or p-ethoxyphenyl, o-, m-, p-(trifluoromethyl)phenyl, o-, m-, p-(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, further preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

In $R^{1'}$ to $R^{4'}$, heteroaryl is taken to mean a saturated or unsaturated mono- or bicyclic heterocyclic radical having 5 to 13 ring members, in which 1, 2 or 3 N and/or 1 or 2 S or O atoms may be present and the heterocyclic radical may be mono- or polysubstituted by $C_1$- to $C_6$-alkyl, C— to $C_6$-alkenyl, —CN, —NO$_2$, F, Cl, Br, I, —OH, —NR'$_2$, —C$_1$-C$_6$-alkoxy, —COOH, —SO$_2$X', —SO$_2$NR'$_2$, —SR", —S(O)R", —SO$_2$R" or SO$_3$H, where X' and R" have a meaning indicated above.

The heterocyclic radical is preferably substituted or nonsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl.

Heteroaryl-$C_1$-$C_6$-alkyl is, analogously to aryl-$C_1$-$C_6$-alkyl, taken to mean, for example, pyridinylmethyl, pyridinylethyl, pyridinylpropyl, pyridinylbutyl, pyridinylpentyl, pyridinylhexyl, where the heterocycles described above may furthermore be linked to the alkylene chain in this way.

$HetN^{z+}$ is preferably

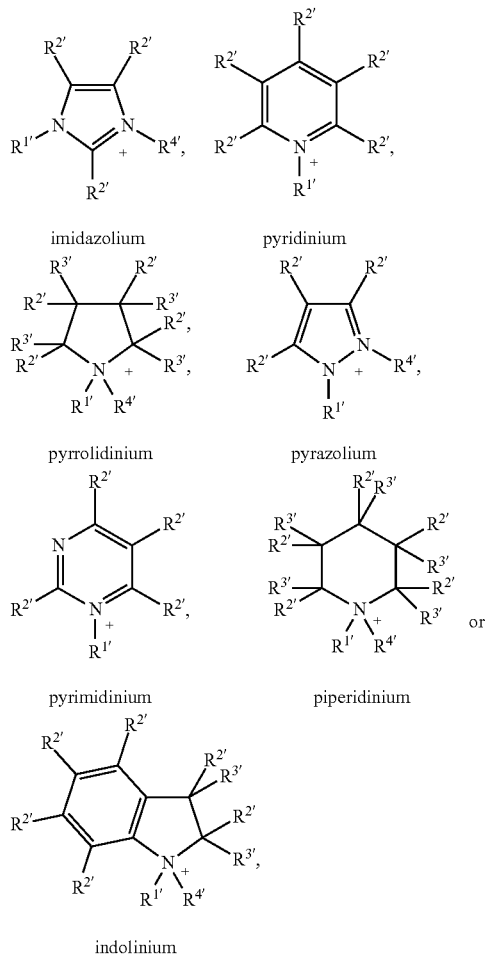

where the substituents $R^{1'}$ to $R^{4'}$ each, independently of one another, have a meaning described above.

$HetN^{z+}$ is particularly preferably

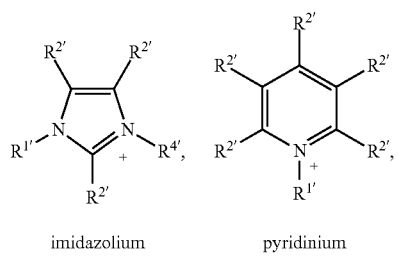

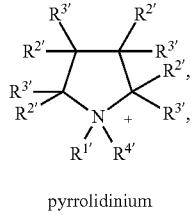

pyrrolidinium where the substituents $R^{1'}$ to $R^{4'}$ each, independently of one another, have a meaning described above.

$HetN^{z+}$ is very particularly preferably

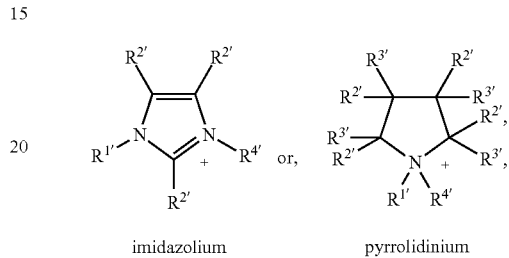

where the substituents $R^{1'}$ to $R^{4'}$ each, independently of one another, have a meaning described above.

Preferred 1,1-dialkylpyrrolidinium cations are, for example, 1,1-dimethylpyrrolidinium, 1-methyl-1-ethylpyrrolidinium, 1-methyl-1-propylpyrrolidinium, 1-methyl-1-butylpyrrolidinium, 1-methyl-1-pentylpyrrolidinium, 1-methyl-1-hexylpyrrolidinium, 1-methyl-1-heptylpyrrolidinium, 1-methyl-1-octylpyrrolidinium, 1-methyl-1-nonylpyrrolidinium, 1-methyl-1-decylpyrrolidinium, 1,1-diethylpyrrolidinium, 1-ethyl-1-propylpyrrolidinium, 1-ethyl-1-butylpyrrolidinium, 1-ethyl-1-pentylpyrrolidinium, 1-ethyl-1-hexylpyrrolidinium, 1-ethyl-1-heptylpyrrolidinium, 1-ethyl-1-octylpyrrolidinium, 1-ethyl-1-nonylpyrrolidinium, 1-ethyl-1-decylpyrrolidinium, 1,1-dipropylpyrrolidinium, 1-propyl-1-methylpyrrolidinium, 1-propyl-1-butylpyrrolidinium, 1-propyl-1-pentylpyrrolidinium, 1-propyl-1-hexylpyrrolidinium, 1-propyl-1-heptylpyrrolidinium, 1-propyl-1-octylpyrrolidinium, 1-propyl-1-nonylpyrrolidinium, 1-propyl-1-decylpyrrolidinium, 1,1-dibutylpyrrolidinium, 1-butyl-1-methylpyrrolidinium, 1-butyl-1-pentylpyrrolidinium, 1-butyl-1-hexylpyrrolidinium, 1-butyl-1-heptylpyrrolidinium, 1-butyl-1-octylpyrrolidinium, 1-butyl-1-nonylpyrrolidinium, 1-butyl-1-decylpyrrolidinium, 1,1-dipentylpyrrolidinium, 1-pentyl-1-hexylpyrrolidinium, 1-pentyl-1-heptylpyrrolidinium, 1-pentyl-1-octylpyrrolidinium, 1-pentyl-1-nonylpyrrolidinium, 1-pentyl-1-decylpyrrolidinium, 1,1-dihexylpyrrolidinium, 1-hexyl-1-heptylpyrrolidinium, 1-hexyl-1-octylpyrrolidinium, 1-hexyl-1-nonylpyrrolidinium, 1-hexyl-1-decylpyrrolidinium, 1,1-dihexylpyrrolidinium, 1-hexyl-1-heptylpyrrolidinium, 1-hexyl-1-octylpyrrolidinium, 1-hexyl-1-nonylpyrrolidinium, 1-hexyl-1-decylpyrrolidinium, 1,1-diheptylpyrrolidinium, 1-heptyl-1-octylpyrrolidinium, 1-heptyl-1-nonylpyrrolidinium, 1-heptyl-1-decylpyrrolidinium, 1,1-dioctylpyrrolidinium, 1-octyl-1-nonylpyrrolidinium, 1-octyl-1-decylpyrrolidinium, 1,1-dinonylpyrrolidinium, 1-nonyl-1-decylpyrrolidinium or 1,1-didecylpyrrolidinium. Very particular preference is given to 1-butyl-1-methylpyrrolidinium or 1-propyl-1-methylpyrrolidinium.

Preferred 1-alkyl-1-alkoxyalkylpyrrolidinium cations are, for example, 1-(2-methoxyethyl)-1-methylpyrrolidinium, 1-(2-methoxyethyl)-1-ethylpyrrolidinium, 1-(2-methoxyethyl)-1-propylpyrrolidinium, 1-(2-methoxyethyl)-1-butylpyrrolidinium, 1-(2-ethoxyethyl)-1-methylpyrrolidinium, 1-ethoxymethyl-1-methylpyrrolidinium. Very particular preference is given to 1-(2-methoxyethyl)-1-methylpyrrolidinium.

Preferred 1,3-dialkylimidazolium cations are, for example, 1-ethyl-3-methylimidazolium, 1-methyl-3-propylimidazolium, 1-methyl-2,3-dimethylimidazolium, 1-ethyl-2,3-dimethylimidazolium, 1-propyl-2,3-dimethylimidazolium, 1-butyl-2,3-dimethylimidazolium, 1-butyl-3-methylimidazolium, 1-methyl-3-pentylimidazolium, 1-ethyl-3-propylimidazolium, 1-butyl-3-ethylimidazolium, 1-ethyl-3-pentylimidazolium, 1-butyl-3-propylimidazolium, 1,3-dimethylimidazolium, 1,3-diethylimidazolium, 1,3-dipropylimidazolium, 1,3-dibutylimidazolium, 1,3-dipentylimidazolium, 1,3-dihexylimidazolium, 1,3-diheptylimidazolium, 1,3-dioctylimidazolium, 1,3-dinonylimidazolium, 1,3-didecylimidazolium, 1-hexyl-3-methylimidazolium, 1-heptyl-3-methylimidazolium, 1-methyl-3-octylimidazolium, 1-methyl-3-nonylimidazolium, 1-decyl-3-methylimidazolium, 1-ethyl-3-hexylimidazolium, 1-ethyl-3-heptylimidazolium, 1-ethyl-3-octylimidazolium, 1-ethyl-3-nonylimidazolium or 1-decyl-3-ethylimidazolium. Particularly preferred cations are 1-ethyl-3-methylimidazolium, 1-butyl-3-methylimidazolium or 1-methyl-3-propylimidazolium.

Preferred 1-alkoxyalkyl-3-alkylimidazolium cations are, for example 1-(2-methoxyethyl)-3-methylimidazolium, 1-(2-methoxyethyl)-3-ethylimidazolium, 1-(2-methoxyethyl)-3-propylimidazolium, 1-(2-methoxyethyl)-3-butylimidazolium, 1-(2-ethoxyethyl)-3-methylimidazolium, 1-ethoxymethyl-3-methylimidazolium.

Preferred 1-alkenyl-3-alkylimidazolium cations are, for example 1-allyl-3-methyl-imidazolium or 1-allyl-2,3-dimethylimidazolium.

Preferred 1-alkyl-pyridinium cations, are for example, 1-methylpyridinium, 1-ethylpyridinium, 1-n-propylpyridinium, 1-isopropylpyridinium, 1-n-butylpyridinium, 1-n-butyl-3-methylpyridinium, 1-n-butyl-4-methylpyridinium, 1-n-butyl-3-ethylpyridinium, 1-n-pentylpyridinium, 1-n-hexylpyridinium, 1-n-heptylpyridinium, 1-n-octylpyridinium, 1-n-nonylpyridinium, 1-n-decylpyridinium, 1-n-undecyl-pyridinium or 1-n-dodecylpyridinium.

The cation [Kt]$^{z+}$ may in addition also be inorganic, in particular a metal cation or NO$^+$. The metal cation may comprise metals from groups 1 to 12 of the Periodic Table.

Preferred metal cations are alkalimetal cations, such as Li$^+$, Na$^+$, K$^+$, Rb$^+$, Cs$^+$, Ag$^+$, Mg$^{2+}$, Cu$^+$, Cu$^{2+}$, Zn$^{2+}$, Ca$^{2+}$, Y$^{+3}$, Yb$^{+3}$, La$^{+3}$, Sc$^{+3}$, Ce$^{+3}$, Ce$^{+4}$, Nd$^{+3}$, Tb$^{+3}$, Sm$^{+3}$ or complex (ligands containing) metal cations which include rare-earths, transitions or noble metals like Rhodium, Ruthenium, Iridium, Palladium, Platinum, Osmium, Cobalt, Nickel, Iron, Chromium, Molybdenium, Tungsten, Vanadium, Titanium, Zirconium, Hafnium, Thorium, Uranium, Gold. The alkalimetal is preferably lithium or potassium. Compounds of formula I in which [Kt]$^{z+}$ is Li$^+$ can be preferably used as conductive salts in primary batteries, secondary batteries, capacitors, supercapacitors or electrochemical cells, optionally also in combination with further conductive salts and/or additives, as constituent of a polymer electrolyte or phase-transfer medium.

Compounds of formula I in which [Kt]$^{z+}$ is K$^+$ can be preferably used as starting materials for compounds of formula I in which [Kt]$^{z+}$ is an organic cation or another metal cation than potassium.

The organic cations of the compounds according to the invention are preferably sulfonium, ammonium, phosphonium cations of formula (1), (3) and (4) or heterocyclic cations of formula (8).

The organic cations of the compounds according to the invention are particularly preferably heterocyclic cations of formula (8) in which HetN$^{z+}$ is imidazolium, pyrrolidinium or pyridinium, as defined above, where the substituents R$^{1'}$ to R$^{4'}$ each, independently of one another, have a meaning described above. The organic cation of the compound of formula (I) is very particularly preferably imidazolium, where the substituents R$^{1'}$ to R$^{4'}$ each, independently of one another, have a meaning described above or has one of the particularly preferred meanings of 1,1-dialkylpyrrolidinium, 1-alkyl-1-alkoxyalkylalkylpyrrolidinium, 1,3-dialkylimidazolium, 1-alkenyl-3-alkylimidazolium or 1-alkoxyalkyl-3-alkylimidazolium as described above.

Particularly suitable organic cations of the formula I are 1-butyl-1-methylpyrrolidinium, 1-ethyl-3-methylimidazolium, 1-ethyl-2,3-dimethylimidazolium, 1-(2-methoxyethyl)-3-methylimidazolium, 1-butyl-3-methylimidazolium, tributyl-methylammonium, tetra-n-butylammonium, tributyl-methylphosphonium, tetra-phenylphosphonium, diethyl-methylsulfonium, S-ethyl-N,N,N',N'-tetramethylisothiouronium, 1-allyl-3-methylimidazolium, 1-allyl-2,3-dimethylimidazolium, 1-cyanomethyl-3-methylimidazolium, 1-methyl-3-propinylimidazlium, 1,1-dimethylpyrrolidinium or trimethylsulfonium.

It goes without saying to the person skilled in the art that substituents, such as, for example, C, H, N, O, Cl, F, in the compounds according to the invention may be replaced by the corresponding isotopes.

The compounds of the formula I in which [Kt]$^{z+}$ is an alkalimetal cation and y is 0 which denotes a compound of formula I-1

[Me]$^+$[B(R$_f$)(CN)$_x$(OR*)$_{3-x}$]$^-$      I-1 in which Me$^+$ is an alkalimetal cation, such as as Li$^+$, Na$^+$, K$^+$, Rb$^+$, Cs$^+$, preferably K$^+$, and R$_f$, x and R* have a meaning as described above can be prepared, for example, by reaction of a compound of formula II

[Me]$^+$[B(R$_f$)(OR*)$_3$]$^-$      II in which [Me]$^+$ has a meaning as defined above and R$_f$ denotes straight-chain or branched perfluoroalkyl groups having 1 to 4 C atoms, C$_6$F$_5$, C$_6$H$_5$, partially fluorinated phenyl or phenyl which is monosubstituted or disubstituted by perfluoroalkyl groups having 1 to 4 C atoms and R* denotes straight-chain or branched alkyl groups having 1 to 4 C atoms with trialkylsilylcyanide in which the alkyl groups independently denotes straight-chain or branched alkyl groups having 1 to 4 C atoms.

Such a reaction of compounds of formula II, as described above, with trialkylsilylcyanide is not described in the literature. The reaction of tetrafluoroborates M[BF$_4$]$^-$ (M=Li$^+$, K$^+$) with trimethylsilyl cyanide,
(CH$_3$)$_3$SiCN, has been studied by E. Bernhard at al. [Z. für Anorg. und Allg. Chem., 629, (2003), p. 677-685]. It was reported that this reaction proceeds very slowly with reaction times of some hours to several weeks and results in the mixtures of dicyanodifluoro-[BF$_2$(CN)$_2$]$^-$ and tricyanofluoroborates [BF(CN)$_3$]$^-$. All attempts to synthesise and isolate monocyanotrifluoroborates [BF$_3$(CN)]$^-$ in this way failed.

Surprisingly, opposite to the reaction with tetrafluoroborates M[BF$_4$]$^-$, the reaction of [R$_F$B(OCH$_3$)$_3$]$^-$ with (CH$_3$)$_3$SiCN proceeds much faster and results in the formation of monocyano- and dicyano-alkoxyborates of formula I as major products. Unexpectedly, trimethylsilylcyanide selectively replaces the alkoxy groups bonded to boron and does not attack the fluorine atoms in the carbon chain of $R_f$.

The invention therefore also relates to a process for the preparation of compounds of the formula I in which $[Kt]^{z+}$ is an alkalimetal cation and y=0 which denotes a compound of formula I-1

$$[Me]^+[B(R_f)(CN)_x(OR^*)_{3-x}]^- \qquad \text{I-1}$$

in which $Me^+$ is an alkalimetal cation and $R_f$, x and $R^*$ have a meaning as described above comprising the reaction of a compound of formula II $$[Me]^+[B(R_f)(OR^*)_3]^- \qquad \text{II}$$

in which $[Me]^+$ has a meaning as defined above and $R_f$ denotes straight-chain or branched perfluoroalkyl groups having 1 to 4 C atoms, $C_6F_5$, $C_6H_5$, partially fluorinated phenyl or phenyl which is monosubstituted or disubstituted by perfluoroalkyl groups having 1 to 4 C atoms and $R^*$ denotes straight-chain or branched alkyl groups having 1 to 4 C atoms with trialkylsilylcyanide in which the alkyl groups independently denotes straight-chain or branched alkyl groups having 1 to 4 C atoms.

This process can be carried out in air, preferably in a dry atmosphere, for example under dry air, nitrogen or argon.

Compounds of formula II are in some cases commercially available or can be synthesized by known processes. Known processes for the preparation of compounds of formula II are described, for example, in A. A. Kolomeitsev, A. A. Kadyrov, J. Szczepkowska-Sztolcman, M. Milewska, H. Koroniak, G. Bissky, J. A. Barten, G.-V. Roschenthaler, Tetrahedron Letters, 44 (2003), p. 8273-8277.; N. Yu. Adonin, V. V. Bardin, H.-J. Frohn, Z. Anorg. Allg. Chem., 633 (2007), p. 647-652.; JP 2008027766 A.

Trialkylsilylcyanide in which the alkyl groups independently denotes straight-chain or branched alkyl groups having 1 to 4 C atoms are in some cases commercially available or can be synthesised by known processes. For example, it is possible to generate trialkylsilylcyanide by the reaction of alkalimetalcyanide with trialkylsilylchloride in the presence of alkalimetaliodide and optionally elemental iodine (M. T. Reetz, I. Chatziiosifidis, Synthesis, 1982, p. 330; J. K. Rasmussen, S. M. Heilmann and L. R. Krepski, The Chemistry of Cyanotrimethylsilane in G. L. Larson (Ed.) "Advances in Silicon Chemistry", Vol. 1, p. 65-187, JAI Press Inc., 1991; WO 2008/102661 A1).

The use of sodium cyanide and sodium iodide or potassium cyanide or potassiumiodide is particular preferred. Preferably, the alkalimetaliodide will be used in 0.1 mol/l related to 1 mol/l alkalicyanide and trialkylsilylchloride. The reaction has to be carried out in a dry atmosphere, for example under dry air, nitrogen or argon.

The alkyl groups of trialkylsilylcyanide may be the same or different. Preferably, they are the same. Examples of trialkylsilylcyanides are such as trimethylsilylcyanide, triethylsilylcyanide, dimethylethylsilylcyanide, triisopropylsilylcyanide, tripropylsilylcyanide or tributylsilylcyanide. Particularly preferred is the use of trimethylsilylcyanide.

The process for the preparation of compounds of the formula I in which $[Kt]^{z+}$ is an alkalimetal cation and y=0 which denotes a compound of formula I-1 as described above may be carried out in an organic solvent or in the absence of an organic solvent if one starting material is liquid at the reaction temperature, at a temperature between 10° C. and 200° C.

Useful organic solvents are for example, acetonitrile, dimethoxyethane or tetrahydrofurane.

In one embodiment of the invention it is preferable to carry out the reaction in a solvent as described above at temperatures between 10° C. and 70° C. to obtain compounds of formula I-1 in which x is 1 as major product if stoichiometric amounts of the compound of formula II and trialkylsilylcyanide are used. The preferred temperature is room-temperature (25° C.). The preferred solvent is tetrahydrofurane.

In another embodiment of the invention it is preferable to carry out the reaction at temperatures between 10° C. and 200° C. in the absence of an organic solvent or in the presence of an organic solvent to obtain compounds of formula I-1 in which x is 2 as major product if more than one equivalent of trialkylsilylcyanide is used. Preferred temperatures are between 60° C. and 100° C., particularly preferred is 70° C. For details, it is referred to the examples. It is preferable, to carry out in the reaction in the absence of an organic solvent.

The following general scheme addresses this issue for compounds of formula I-1 in which Me is potassium:

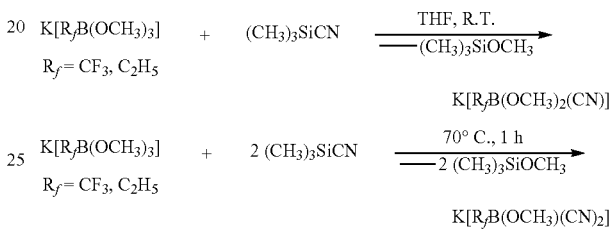

The compounds of the formula I-1 in which x=2 can alternatively be synthesised, for example, by reaction of compounds of formula II with trialkylsilylcyanide at temperatures between 10° C. and 30° C., particularly at room-temperature, but with reaction times about some days, e.g. 3 days as described in example 4 instead of some hours.

The compounds of the formula I-1 in which x=2 can in addition alternatively be synthesised, for example, by reaction of compounds of formula IV $$[Me]^+[B(R_f)F_3]^- \qquad \text{IV}$$

in which $[Me]^+$ has a meaning as defined above and $R_f$ denotes straight-chain or branched perfluoroalkyl groups having 1 to 4 C atoms or $C_6F_5$, $C_6H_5$, partially fluorinated phenyl or phenyl which is monosubstituted or disubstituted by perfluoroalkyl groups having 1 to 4 C atoms with trialkylsilylcyanide in which the alkyl groups independently denotes straight-chain or branched alkyl groups having 1 to 4 C atoms and alkoxytrimethylsilane in which alkoxy has the same meaning as $R^*O$ of the compound of formula I-1.

The compounds of formula IV are in some cases commercially available or can be synthesised by known processes. Known processes for the preparation of compounds of formula IV are described, for example, in U.S. Pat. No. 7,208, 626 B2; WO 2003/087020 (A1) and WO 2003/087113 (A1) or in R. D. Chambers et al., J. Am. Chem. Soc. 82 (1960), p. 5296-5301; H.-J-Frohn and V. V. Bardin, Z. für Anorg. und Allg. Chemie, 627 (2001), S. 15-16; G. A. Molander and G. P. Hoag, Organometallics, 22 (2003), p. 3313-3315 or Zhi-Bin Zhou et al., J. of Fluorine Chem., 123 (2003), p. 127-131]. The process for the preparation of compounds of the formula I-1 through reaction of a compound of formula IV with trialkylsilylcyanide with x=2 as described above may be carried out in an organic solvent or in the absence of an organic solvent if one starting material is liquid at the reaction temperature, at a temperature between 10° C. and 100° C., preferably between 10° and 30° C., particularly preferably at room-temperature and in a protective gas-atmosphere. It is preferred to carry out this process in the absence of an organic solvent.

Useful organic solvents are for example, acetonitrile, dimethoxyethane or tetrahydrofurane, The invention, in addition, also relates to a process for the preparation of compounds of the formula I in which $[Kt]^{z+}$ is an alkalimetal cation and y=1 and x=1 which denotes a compound of formula I-2

$$[Me]^+[B(R_f)(CN)(OR^*)F]^{-/2}$$

in which $Me^+$ is an alkalimetal cation and $R_f$ and $R^*$ have a meaning as described above comprising the reaction of a compound of formula III $$[Me]^+[B(R_f)(OR^*)F_2]^- \qquad \text{III}$$

in which $[Me]^+$ has a meaning as defined above and $R_f$ denotes straight-chain or branched perfluoroalkyl groups having 1 to 4 C atoms, $C_6F_5$, $C_6H_5$, partially fluorinated phenyl or phenyl which is monosubstituted or disubstituted by perfluoroalkyl groups having 1 to 4 C atoms and $R^*$ denotes straight-chain or branched alkyl groups having 1 to 4 C atoms with trialkylsilylcyanide in which the alkyl groups independently denotes straight-chain or branched alkyl groups having 1 to 4 C atoms.

Also this process preferably should be carried out in a dry atmosphere, for example under dry air, nitrogen or argon.

Compounds of formula III may be synthesized via methods based on N. Yu. Adonin, H.-J. Frohn, V. V. Bardin, *Organometallics*, 26 (2007), p. 2420-2425; G. A. Molander, B. P. Hoag, *Organometallics*, 22 (2003), p. 3313-3315.

The process for the preparation of compounds of the formula I in which $[Kt]^{z+}$ is an alkalimetal cation and y=1 and x=1 which denotes a compound of formula I-2 as described above may be carried out in an organic solvent or in the absence of an organic solvent if one starting material is liquid at the reaction temperature, at a temperature between 10° C. and 200° C.

In both processes as described above for compounds of formulae I-1 or I-2, it is possible and sometimes preferable to generate trialkylsilylcyanide in situ before addition of the compound of formulae II or III. This in-situ generation may be carried out under the reaction conditions as described before.

The process for the preparation of compounds of formula I in which the cation is an organic cation or an inorganic cation other than an alkalimetal cation is a metathesis reaction (salt-exchange reaction) in which the cation will be replaced as commonly known.

The invention therefore also relates to a process for the preparation of a compound of formula I in which $[Kt]^{z+}$ is another cation than an alkalimetal cation in a salt-exchange reaction as described above, characterized in that an alkalimetal salt of formula I-1

$$[Me]^+[B(R_f)(CN)_x(OR^*)_{3-x}]^- \qquad \text{I-1 or of formula I-2}$$

$$[Me]^+[B(R_f)(CN)(OR^*)(F)]^- \qquad \text{I-2}$$

in which Me is an alkalimetal cation or $H^+$ and $R_f$, x, and $R^*$ have a meaning as described above is reacted with a compound of formula V $$KtA \qquad \text{V,}$$

in which
Kt has a meaning of an organic cation or a metal cation other than the alkalimetal cation of the compound of formula I-1 or formula I-2 and A denotes $F^-$, $Cl^-$, $Br^-$, $I^-$, $OH^-$, $[HF_2]^-$, $[CN]^-$, $[SCN]^-$, $[R_1COO]^-$, $[R_1SO_3]^-$, $[R_2COO]^-$, $[R_2SO_3]^-$, $[R_1OSO_3]^-$, $[SiF_6]^{2-}$, $[BF_4]^-$, $[SO_4]^{2-}$, $[HSO_4]^{1-}$, $[NO_3]^-$, $[(R_2)_2P(O)O]^-$, $[R_2P(O)O_2]^{2-}$, tosylate, benzoate, oxalate, succinate, suberate, ascorbate, sorbate, tartrate, citrate, malate, malonate, the malonate optionally substituted with straight-chain or branched alkyl groups having 1 to 4 C atoms or $[CO_3]^{2-}$, in which $R_1$ is each indepentantly of another H or a straight-chain or branched alkyl group having 1 to 12 C atoms and $R_2$ is each independently of one another a straight-chain or branched fluorinated or perfluorinated alkyl group having 1 to 12 C atoms or pentafluorophenyl and where electroneutrality should be taken into consideration in the formula of the salt KtA.

$R_2$ is particularly preferred trifluoromethyl, pentafluoroethyl or nonafluorobutyl, very particularly preferred trifluoromethyl or pentafluoroethyl.

$R_1$ is particularly preferred methyl, ethyl, n-butyl, n-hexyl or n-octyl, very particularly preferred methyl or ethyl.

Substituted malonates are for example methyl malonate or ethyl malonate.

The compounds of formula V are in most cases commercially available or can be synthesised by known processes. Known processes for the preparation of compounds of formula V are described, for example, in P.

Wasserscheid, T. Welton (Eds.), Ionic Liquids in Synthesis, Second Edition, WILEY-VCH, Weinheim, 2008.

The anion in the formula V is preferably $F^-$, $Cl^-$, $Br^-$, $I^-$, $[HF_2]^-$, $[CN]^-$, $[SCN]^-$, $[CH_3COO]^-$, $[CH_3SO_3]^-$, $[CF_3COO]^-$, $[CF_3SO_3]^-$, $[CH_3OSO_3]^-$, $[SiF_6]^{2-}$, $[BF_4]^-$, $[SO_4]^{2-}$, $[NO_3]^-$, $[C_2H_5OSO_3]^-$, $[(C_2F_5)_2P(O)O]^-$, $[C_2F_5P(O)O_2]^{2-}$, tosylates, malonates or $[CO_3]^{2-}$, particularly preferably $OH^-$, $Cl^-$, $Br^-$, $I^-$, $[CH_3SO_3]^-$, $[CH_3OSO_3]^-$, $[CF_3COO]^-$, $[CF_3SO_3]$, $[(C_2F_5)_2P(O)O]^-$ or $[CO_3]^{2-}$, very particularly preferably $OH^-$, $Cl^-$, $Br^-$, $[CH_3OSO_3]^-$, $[CF_3SO_3]^-$, $[CH_3SO_3]^-$ or $[(C_2F_5)_2P(O)O]^-$.

Suitable organic salts for the preparation of the compounds of the formula I in which $[Kt]^{z+}$ is an organic cation are salts cations of formulae (1) to (8) or their preferred embodiments together with anions as defined as A described above or its preferred embodiments which means salts of cations of formulae (1) to (8) or their preferred embodiments and $OH^-$, $Cl^-$, $Br^-$, $[CH_3OSO_3]^-$, $[CF_3SO_3]^-$, $[CH_3SO_3]^-$ or $[(O_2F_5)_2P(O)O]^-$.

Suitable inorganic salts for the preparation of the compounds of the formula I in which $[Kt]^{z+}$ is a metal cation e.g. from the group silver, magnesium, copper, zinc and calcium are, for example, $Ag_2O$, $Ag_2CO_3$, $MgCO_3$, $CuO$, $ZnO$, $Zn[HCO_3]_2$, $CaCO_3$ or $Ca(CO_2CH_3)_2$. Useful salts for metathesis reaction to another alkalimetal salt than potassium are e.g. $LiBF_4$, or for the reaction with compounds of the formula I in which $[Kt]^{z+}=H^+$—$Na_2CO_3$, $NaOH$, $Li_2CO_3$, $LiOH$, $Li(CO_2CH_3)$, $Rb_2CO_3$, $RbOH$, $Cs_2CO_3$, or $CsOH$.

The reaction is advantageously carried out in water, where temperatures of 10°-100° C., preferably 15°-60° C., particularly preferably room temperature, are suitable.

However, the reaction can alternatively also be carried out in organic solvents at temperatures between 10 and 100° C. Suitable solvents here are acetonitrile, dioxane, dichloromethane, dimethoxyethane or an alcohol, for example methanol or ethanol.

In a special embodiment of this salt-exchange reaction it is possible to use the compounds of formulae I-1 or I-2 directly after their synthesis as crude materials without purified isolation. It preferred to separate volatile side products such as the reaction products trialkylsilylfluoride and alkoxytrialkylsilanes or the excess of trialkylsilylcyanide and to use the crude material for the salt-exchange reaction.

The present invention furthermore relates to the use of the compounds of formula I with organic cations being ionic liquids as described in detail above as solvent or solvent additive, as phase-transfer catalyst, as extractant, as heat-transfer medium, as surface-active substance, as plasticiser, as flame retardant, as conductive salt or additive in electrochemical cells.

In the case of the use of the said ionic liquids of formula I as solvents, these are suitable in any type of reaction known to the person skilled in the art, for example for transition-metal- or enzyme-catalysed reactions, such as, for example, hydroformylation reactions, oligomerisation reactions, esterifications or isomerisations, where the said list is not exhaustive.

On use as extractant, the ionic liquids of formula I can be employed to separate off reaction products, but also to separate off impurities, depending on the solubility of the respective component in the ionic liquid. In addition, the ionic liquids may also serve as separation media in the separation of a plurality of components, for example in the distillative separation of a plurality of components of a mixture.

Further possible applications are the use as plasticiser in polymer materials, as flame retardant for a number of materials or applications, and as conductive salt or additive in various electrochemical cells and applications, for example in galvanic cells, in capacitors or in fuel cells.

Further fields of applications of the ionic liquids of formula I, according to this invention are solvents for carbohydrate containing solids in particular biopolymers and derivatives or degradation products thereof. In addition, these new compounds can be applied as lubricants, working fluids for machines, such as compressors, pumps or hydraulic devices. A further field of application is the field of particle or nanomaterial synthesis where these ionic liquids can act as medium or additive.

The compounds of formula I with organic cations, e.g. ionic liquids according to this invention may be preferably used in electrochemical and/or optoelectronic devices, especially in electrolyte formulations.

The present invention therefore relates furthermore to an electrolyte formulation comprising at least one compound of formula I as described above or preferably described.

Electrolyte formulations of compounds of formula I in which $[Kt]^{z+}$ is $Li^+$ or an organic cation can be preferably used in primary batteries, secondary batteries, capacitors, supercapacitors or electrochemical cells, optionally also in combination with further conductive salts and/or additives, as constituent of a polymer electrolyte or phase-transfer medium. Preferred batteries are lithium batteries or lithiumion batteries. A preferred capacitor is a lithiumion capacitor.

Electrolyte formulations of compounds of formula I can be preferably used in electrochemical and/or optoelectronic devices such as a photovoltaic cell, a light emitting device, an electrochromic or photo-electrochromic device, an electrochemical sensor and/or biosensor, particularly preferred in a dye sensitised solar cell.

Such electrolyte formulations form a crucial part of the disclosed devices and the performance of the device largely depends on the physical and chemical properties of the various components of these electrolytes.

Electrolyte formulations according to the invention are alternatives to already known electrolyte formulations. They show especially in the field of electrolyte formulations of dye sensitised solar cells an increased power conversion efficiency particularly under low temperature. The advantage of the use of e.g. perfluoroalkylcyanomethoxyfluoroborate is their low viscosity, and subsequently the smaller Nernst diffusion resistance of the oxidant species especially, at lower temperature.

WO 2007/093961 and WO 2009/083901 describe so far the best power conversion efficiencies in ionic liquid-based electrolytes containing a significant quantity of organic salts with tetracyanoborate (TCB) anions.

In chemistry, an electrolyte is any substance containing free ions that make the substance electrically conductive. The most typical electrolyte is an ionic solution, but molten electrolytes and solid electrolytes are also possible.

An electrolyte formulation according to the invention is therefore an electrically conductive medium, basically due to the presence of at least one substance that is present in a dissolved and or in molten state i.e. supporting an electric conductivity via motion of ionic species.

Typical molar concentrations of the inventive anion of formula Ia as described above in the electrolyte formulations range from 0.1 to 3 M, preferably from 0.8 to 3 M. This molar concentration in the electrolyte may be achieved with one or more compounds of formula (I) in which $[Kt]^{z+}$ is an inorganic or an organic cation.

Preferably, the molar concentration is achieved with at least one compound of formula I in which $[Kt]^{z+}$ is an organic cation as described or preferably described above.

For the purpose of the present invention, the molar concentration refer to the concentration at 25° C.

Preferably, the electrolyte formulation according to the invention comprise at least one compound of formula (I) in which $[Kt]^{z+}$ is a cation selected from cations of formulae (1), (3), (4), (6) or (8) as defined or particularly preferably described.

Particularly preferably, the electrolyte formulation according to the invention comprises at least one compound of formula (I) in which $[Kt]^{z+}$ is a cation selected from cations of formula (1) or (8) as defined or particularly preferably described.

Very particularly preferably, the electrolyte formulation according to the invention comprises at least one compound of formula (I) in which $[Kt]^{z+}$ is a cation selected from cations of formula (1) as defined or particularly preferably described.

Very particularly preferably, the electrolyte formulation according to the invention comprises at least one compound of formula (I) in which $[Kt]^{z+}$ is a cation selected from cations of formula (8) as defined or particularly preferably described.

Other components of the electrolyte formulation are one or several further salts, solvents, iodine and others, as indicated further below.

If the electrolyte formulation is a binary system, it comprises two salts, one further salt and a compound of formula (I) as described above. If the electrolyte formulation is a ternary system, it comprises two further salts and a compound of formula (I) as described above. The binary system comprises 90-20 weight %, preferably 80-55 weight %, more preferably 70-60 weight % of the further salt and 10-80 weight %, preferably 20-45 weight % or more preferably 30-40 weight % of the compound of formula (I) as described above. The percentages in this paragraph are expressed with respect to the total of salts (=100 weight %) present in the electrolyte formulation according to the invention. Amounts of further, generally optional components (additives) indicated below, such as N-containing compounds having unshared electron pairs, iodine, solvents, polymers, and nanoparticles, for example, are not considered therein. The same percentages apply to ternary or quaternary systems which means the total of the further salts has to be used in the given ranges, e.g. two further ionic liquids are comprised in e.g. 90-20 weight. % in the electrolyte formulation according to the invention.

According to another embodiment of the present invention, the electrolyte formulation comprises at least one further salt with organic cations comprising a quaternary nitrogen and an anion selected from a halide ion, such as F⁻, Cl⁻, I⁻, a polyhalide ion, a fluoroalkanesulfonate, a fluoroalkanecarboxylate, a tri(fluoroalkylsulfonyl)methide, a bis(fluoroalkylsulfonyl)imide, a nitrate, a hexafluorophosphate, a tris-, bis- and mono-(fluoroalkyl)fluorophosphate, a tetrafluoroborate, a dicyanamide, a tricyanomethide, a tetracyanoborate, a thiocyanate, an alkylsulfonate or an alkylsulfate, with fluoroalkane having 1 to 20 C atoms, preferably perfluorinated, fluoroalkyl having 1 to 20 C atoms and alkyl having 1 to 20 C atoms. Fluoroalkane or fluoroalkyl is preferably perfluorinated.

Preferably, the further salts are selected from salts comprising anions such as iodide, thiocyanate or tetracyanoborate, particularly preferred further salts are iodides.

The cation of the at least one further salt or of a preferred further salt may be selected amongst organic compounds comprising a quaternary nitrogen atom, preferably cyclic organic cations such as pyridinium, imidazolium, triazolium, pyrrolidinium or morpholinium.

However, to limit the amount of different cations in the electrolyte formulations, especially for DSC, the organic cations may be selected from the definitions for the cations of the compounds of formula I. Therefore, according to another preferred embodiment of the present invention, the electrolyte formulation comprises at least one compound of formula I as described above and at least one further iodide in which the organic cations are independently selected from the group of

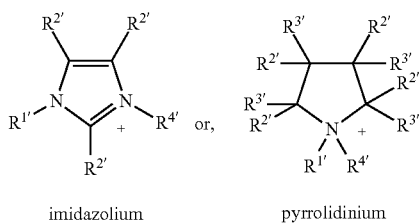

imidazolium          pyrrolidinium in which the substituents $R^{1'}$ to $R^{4'}$ have a meaning as described or preferably described above.

Particularly preferred examples of the at least one further salt are 1-ethyl-3-methylimidazolium iodide, 1-propyl-3-methylimidazolium iodide, 1-butyl-3-methyl-imidazolium iodide, 1-hexyl-3-methylimidazolium iodide, 1,3-dimethylimidazolium iodide, 1-allyl-3-methylimidazolium iodide, N-butyl-N-methyl-pyrrolidinium iodide or N,N-dimethyl-pyrrolidinium iodide.

In another embodiment of the invention, guanidinium thiocyanate may be added to the electrolyte formulation according to the invention.

The electrolyte formulation of the invention preferably comprises iodine ($I_2$).

Preferably, it comprises from 0.01 to 50 weight %, more preferably 0.1 to 20 weight % and most preferably from 1 to 10 weight % of $I_2$.

In a preferred embodiment, the electrolyte formulation of the present invention further comprises at least one compound containing a nitrogen atom having non-shared electron pairs. Examples of such compounds are found in EP 0 986 079 A2, starting on page 2, lines 40-55, and again from page 3, lines 14 extending to page 7, line 54, which are expressly incorporated herein by reference. Preferred examples of compounds having non-shared electron pairs include imidazole and its derivatives, particularly benzimidazole and its derivatives.

The electrolyte formulation of the present invention comprises less than 50% of an organic solvent. Preferably, the electrolyte formulation comprises less than 40%, more preferably less than 30%, still more preferably less than 20% and even less than 10%. Most preferably, the electrolyte formulation comprises less than 5% of an organic solvent. For example, it is substantially free of an organic solvent. Percentages are indicated on the basis of weight %.

Organic solvents, if present in such amounts as indicated above, may be selected from those disclosed in the literature. Preferably, the solvent, if present, has a boiling point higher than 160 degrees centigrade, more preferably higher than 190 degrees such as propylene carbonate, ethylene carbonate, N-methyloxazolidinone, N,N'-dimethylimidazolidinone, tetraglyme and methoxy-substituted nitriles or sulfones which are preferably asymmetrically substituted such as 2-ethanesulfonyl-propane, 1-ethanesulfonyl-2-methyl-propane or 2-(propane-2-sulfonyl)-butane.

If a solvent is present in the electrolyte formulation, there may further be comprised a polymer as gelling agent, wherein the polymer is polyvinylidenefluoride, polyvinylidene-hexafluoropropylene, polyvinylidene-hexafluoropropylene-chlorotrifluoroethylene copolymers, nafion, polyethylene oxide, polymethylmethacrylate, polyacrylonitrile, polypropylene, polystyrene, polybutadiene, polyethyleneglycol, polyvinylpyrrolidone, polyaniline, polypyrrole, polythiophene. The purpose of adding these polymers to electrolyte formulations is to make liquid electrolytes into quasi-solid or solid electrolytes, thus improving solvent retention, especially during aging.

The electrolyte formulation of the invention may further comprise metal oxide nanoparticles like $SiO_2$, $TiO_2$, $Al_2O_3$, MgO or ZnO, for example, which are also capable of increasing solidity and thus solvent retention.

The electrolyte formulation of the invention has many applications. For example, it may be used in an optoelectronic and/or electrochemical device such as a photovoltaic cell, a light emitting device, an electrochromic or photo-electrochromic device, an electrochemical sensor and/or biosensor. Also the use in electrochemical batteries is possible, for example in a lithium ion battery or a double layer capacitor.

The present invention therefore relates further to the use of the electrolyte formulation as described in detail above in an electrochemical and/or optoelectronic device which is a photovoltaic cell, a light emitting device, an electrochromic or photo-electrochromic device, an electrochemical sensor and/or biosensor. Preferably, the electrolyte formulation may be used in dye sensitized solar cells.

The present invention therefore relates furthermore to an electrochemical and/or optoelectronic device, for example a photovoltaic cell, a light emitting device, an electrochromic or photo-electrochromic device, an electrochemical sensor and/or biosensor comprising an electrolyte formulation comprising at least one compound of formula I $$[Kt]^{z+}z[B(R_f)(CN)_x(OR^*)_{3-x-y}(F)_y]^- \quad \text{I}$$

in which $[Kt]^{z+}$ denotes an inorganic or organic cation,
z is 1 or 2,
x is 1 or 2, y is 0 or 1 and x+y is <3,
$R_f$ denotes straight-chain or branched perfluoroalkyl groups having 1 to 4 C atoms, $C_6F_5$, $C_6H_5$, partially fluorinated phenyl or phenyl which is monosubstituted or disubstituted by perfluoroalkyl groups having 1 to 4 C atoms and R* denotes straight-chain or branched alkyl groups having 1 to 4 C atoms or a preferred embodiment of such a compound of formula I as described above.

According to a preferred embodiment, the device of the resent invention is a dye or quantum dot sensitized solar cell, particularly preferably a dye sensitized solar cell.

Quantum dot sensitized solar cells are disclosed in U.S. Pat. No. 6,861,722, for example. In dye-sensitized solar cells, a dye is used to absorb the sunlight to convert into the electrical energy. Examples of dyes are disclosed in EP 0 986 079 A2, EP 1 180 774 A2 or EP 1 507 307 A1.

Preferred dyes are Z907 or Z907Na which are both an amphiphilic ruthenium sensitizer.

In a preferred embodiment, the dye is coadsorbed with a phosphinic acid. A preferred example of a phosphinic acid is bis(3,3-dimethyl-butyl)-phosphinic acid (DINHOP) as disclosed in M. Wang et al, Dalton Trans., 2009, 10015-10020.

The dye Z907Na means NaRu(2,2'-bipyridine-4-carboxylic acid-4'-carboxylate)(4,4'-dinonyl-2,2'-bipyridine)(NCS)$_2$.

For example, a dye-sensitized solar cell comprises a photoelectrode, a counter electrode and, between the photoelectrode and the counterelectrode, an electrolyte formulation or a charge transporting material, and wherein a sensitizing dye is absorbed on the surface of the photoelectrode, on the side facing the counterelectrode.

According to a preferred embodiment of the device according to the invention, it comprises a semiconductor, the electrolyte formulation as described above and a counter electrode.

According to a preferred embodiment of the invention, the semiconductor is based on material selected from the group of Si, TiO$_2$, SnO$_2$, Fe$_2$O$_3$, WO$_3$, ZnO, Nb$_2$O$_5$, CdS, ZnS, PbS, Bi$_2$S$_3$, CdSe, GaP, InP, GaAs, CdTe, CuInS$_2$, and/or CuInSe$_2$. Preferably, the semiconductor comprises a mesoporous surface, thus increasing the surface optionally covered by a dye and being in contact with the electrolyte. Preferably, the semiconductor is present on a glass support or plastic or metal foil. Preferably, the support is conductive.

The device of the present invention preferably comprises a counter electrode. For example, fluorine doped tin oxide or tin doped indium oxide on glass (FTO- or ITO-glass, respectively) coated with Pt, carbon of preferably conductive allotropes, polyaniline or poly(3,4-ethylenedioxythiophene) (PEDOT). Metal substrates such as stainless steel or titanium sheet may be possible substrates beside glass.

The device of the present invention may be manufactured as the corresponding device of the prior art by simply replacing the electrolyte by the electrolyte formulation of the present invention. For example, in the case of dye-sensitized solar cells, device assembly is disclosed in numerous patent literature, for example WO 91/16719 (examples 34 and 35), but also scientific literature, for example in Barbé, C. J., Arendse, F., Comte, P., Jirousek, M., Lenzmann, F., Shklover, V., Gratzel, M. J. Am. Ceram. Soc. 1997, 80, 3157; and Wang, P., Zakeeruddin, S. M., Comte, P., Charvet, R., Humphry-Baker, R., Grätzel, M. J. Phys. Chem. B 2003, 107, 14336.

Preferably, the sensitized semiconducting material serves as a photoanode. Preferably, the counter electrode is a cathode.

The present invention provides a method for preparing a photoelectric cell comprising the step of bringing the electrolyte formulation of the invention in contact with a surface of a semiconductor, said surface optionally being coated with a sensitizer. Preferably, the semiconductor is selected from the materials given above, and the sensitizer is preferably selected from quantum dots and/or a dye as disclosed above, particularly preferably selected from a dye.

Preferably, the electrolyte formulation may simply be pured on the semiconductor. Preferably, it is applied to the otherwise completed device already comprising a counter electrode by creating a vacuum in the internal lumen of the cell through a hole in the counter electrode and adding the electrolyte formulation as disclosed in the reference of Wang et al., J. Phys. Chem. B 2003, 107, 14336.

Even without further comments, it is assumed that a person skilled in the art will be able to utilise the above description in the broadest scope. The preferred embodiments and examples should therefore merely be regarded as descriptive disclosure which is absolutely not limiting in any way.

The synthesized compounds are characterized through Raman spectroscopy, NMR spectroscopy or elemental analysis. The NMR spectrum is measured in acetone-D6 (Bruker Avance III with deuterium as lock). Used frequencies: $^1$H: 400.17 MHz, $^{19}$F: 376.54 MHz, $^{11}$B: 128.39 MHz, $^{31}$P: 161.99 MHz and $^{13}$C: 100.61 MHz, external references: TMS for $^1$H and $^{13}$C; CCl$_3$F— for $^{19}$F and BF$_3$.Et$_2$O— for $^{11}$B.

Data for the anion [C$_2$F$_5$B(OCH$_3$)(CN)$_2$]$^-$ in the synthesized ionic liquids:

$^{13}$C-NMR (solvent: acetone-D$_6$ and reference):

$^{13}$C{$^1$H}-NMR: δ, ppm=129.21 q (2CN, 2C); 122.10 q, t (CF$_3$, 1C); 118.0 m (CF$_2$, 1C); 53.37 s (OCH$_3$, 1C).

EXAMPLE 1

Potassium cyanodimethoxytrifluoromethylborate— K[CF$_3$B(OCH$_3$)$_2$(CN)]

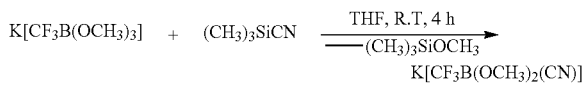

Potassium trimethoxytrifluoromethylborate, K[CF$_3$B(OCH$_3$)$_3$] (1.7 g, 8.1 mmol), is weighed out into a cylindrical reaction vessel with a glass valve and PTFE spindle (Young, London) and a magnetic stirrer bar. THF (10 ml) and trimethylsilyl cyanide (1.1 ml, 8.1 mmol) are added under an argon atmosphere. The reaction mixture is stirred at room temperature for 4 hours. The reaction volume is subsequently reduced to 2 ml, and K[CF$_3$B(OCH$_3$)$_2$CN] is precipitated by slow addition of CH$_2$Cl$_2$ (25 ml), filtered off under inert conditions and dried in vacuo. The yield of pale-beige potassium cyanodimethoxytrifluoromethylborate is 1.3 g (6.33 mmol), 79% based on the potassium trimethoxytrifluoromethylborate employed. The product is characterized by NMR-spectroscopy in THF-D$_8$:

$^1$H{$^{11}$B}-NMR: δ, ppm=3.32 s (2OCH$_3$, 6H);

$^{11}$B{$^1$H}-NMR: δ, ppm=−3.0 q (1B), $^2J_{F,B}$=23.2 Hz;

$^{19}$F{$^1$H}-NMR: δ, ppm=−72.62 q (CF$_3$, 3F), $^2J_{F,B}$=25-31 Hz;

$^{13}$C{$^1$H}-NMR: δ, ppm=~134 qq (CF$_3$, 1C); 131.1 q (CN, 1C); 51.3 s (2OCH$_3$, 2C).

EXAMPLE 2

Potassium dicyanomethoxytrifluoromethylborate—
K[CF$_3$B(OCH$_3$)(CN)$_2$]

A.

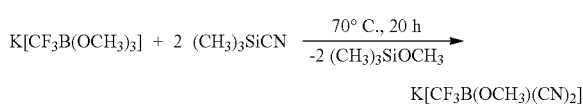

Potassium trimethoxytrifluoromethylborate, K[CF$_3$B(OCH$_3$)$_3$] (6.0 g, 28.3 mmol), is weighed out into a cylindrical reaction vessel with a glass valve and PTFE spindle (Young, London) and a magnetic stirrer bar. Trimethylsilyl cyanide (25.0 ml, 187.5 mmol) is added in vacuo. The reaction mixture is stirred at 70° C. for 20 hours. All volatile constituents are removed in vacuo. The unreacted trimethylsilyl cyanide is recovered as a mixture with trimethylmethoxysilane and can be employed for further reactions. The residue is dissolved in acetonitrile (5 ml). Addition of CHCl$_3$ (400 ml) causes the precipitation of virtually colourless K[CF$_3$B(OCH$_3$)(CN)$_2$], which is filtered off and dried in vacuo. The yield of potassium dicyanomethoxytrifluoromethylborate is 4.9 g (24.3 mmol), 86% based on the potassium trimethoxytrifluoromethylborate employed. Decomposition from 200° C.; Raman spectroscopy: ν (CN)=2217 cm$^{-1}$. The product is characterized by NMR-spectroscopy:

$^{11}$B{$^{1}$H}-NMR: δ, ppm=−13.5 q (1B), $^2J_{F,B}$=33.3 Hz.

$^{19}$F{$^{1}$H}-NMR: δ, ppm=−71.2 q (CF$_3$, 3F), $^2J_{F,B}$=33.4 Hz.

B.

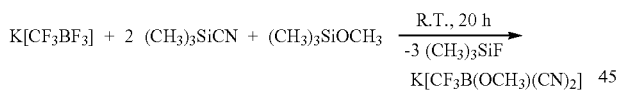

Potassium trifluorotrifluoromethylborate, K[CF$_3$BF$_3$] (0.19 g, 1.1 mmol), is weighed out into a cylindrical reaction vessel with a glass valve and PTFE spindle (Young, London) and a magnetic stirrer bar. A mixture of trimethylsilyl cyanide and methoxytrimethylsilane (10 ml, ~10:1 v/v) is condensed into the flask. The reaction mixture is stirred at room temperature for 20 hours. All volatile constituents are removed in vacuo, and the majority of the mixture of unreacted trimethylsilyl cyanide and trimethylmethoxysilane is recovered. The residue is dissolved in acetonitrile (1 ml), and addition of CHCl$_3$ (50 ml) causes the precipitation of virtually colourless K[CF$_3$B(OCH$_3$)(CN)$_2$], which is dried in vacuo. The yield of potassium dicyanomethoxytrifluoromethylborate is 0.17 g (0.8 mmol), 75% based on the potassium trifluorotrifluoromethylborate employed. The NMR spectra of the obtained product are conside with spectra described in the Example 2A.

EXAMPLE 3

Potassium cyanodimethoxypentafluoroethylborate—
K[C$_2$F$_5$B(OCH$_3$)$_2$(CN)]

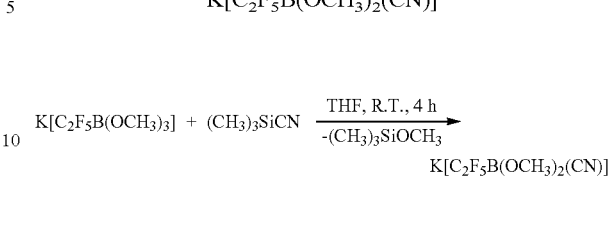

Potassium trimethoxypentafluoroethylborate, K[C$_2$F$_5$B(OCH$_3$)$_3$] (1.0 g, 3.8 mmol), is weighed out into a cylindrical reaction vessel with a glass valve and PTFE spindle (Young, London) and a magnetic stirrer bar. THF (5 ml) and then trimethylsilyl cyanide (0.5 ml, 4.0 mmol) are added under a protective-gas atmosphere. The reaction mixture is stirred at room temperature for 4 hours and subsequently evaporated to dryness. The residue is dissolved in acetonitrile (5 ml). Addition of CHCl$_3$ (100 ml) causes the formation of a fine precipitate of virtually colourless potassium cyano-dimethoxypentafluoroethylborate, K[C$_2$F$_5$B(OCH$_3$)$_2$(CN)], which is filtered off under inert conditions and dried in vacuo. The yield of K[C$_2$F$_5$B(OCH$_3$)$_2$(CN)] is 0.95 g (3.7 mmol), 97% based on the potassium trimethoxypentafluoroethylborate employed. The product is characterized by NMR-spectroscopy in THF-D$_8$:

$^{1}$H{$^{11}$B}-NMR: δ, ppm=3.34 s (2OCH$_3$, 6H);

$^{11}$B{$^{1}$H}-NMR: δ, ppm=−2.2 t (1B), $^2J_{F,B}$=18.8 Hz;

$^{19}$F{$^{1}$H}-NMR: δ, ppm=−82.86 s (CF$_3$, 3F); −131.12 q (CF$_2$, 2F), $^2J_{F,B}$=17-20 Hz;

$^{13}$C{$^{1}$H}-NMR: δ, ppm=131.0 q (CN, 1C); 124.2 qt (CF$_3$, 1C); 122.0 m (CF$_2$, 1C); 51.5 s (2OCH$_3$, 2C).

EXAMPLE 4

Potassium dicyanomethoxypentafluoroethylborate—
K[C$_2$F$_5$B(OCH$_3$)(CN)$_2$]

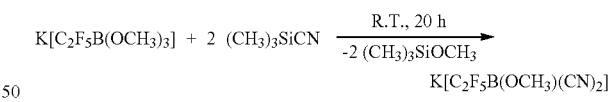

Potassium trimethoxypentafluoroethylborate, K[C$_2$F$_5$B(OCH$_3$)$_3$] (20.0 g, 76.3 mmol), is weighed out into a 500 ml reaction vessel with a glass valve and PTFE spindle (Young, London) and a magnetic stirrer bar. The flask is secured, and trimethylsilyl cyanide (80.0 ml, 600 mmol) recycled from previous experiments (contains 20% methoxytrimethylsilan, (CH$_3$)$_3$SiOCH$_3$) is added under argon. The reaction mixture is stirred at room temperature for 20 hours. All volatile constituents are removed in vacuo. The unreacted trimethylsilyl cyanide is recovered as a mixture with trimethylmethoxysilane and can be employed for further reactions. The residue is dissolved in 30% aqueous H$_2$O$_2$ (100 ml), and K$_2$CO$_3$ (20.0 g) is added to the solution with stirring. The mixture is left stirring for 2 hours at room temperature and is treated with potassium disulfite K$_2$S$_2$O$_5$ until negative test to peroxide (Peroxid-Test Merckoquant®). The mixture is extracted with THF (6×50 ml). The combined organic phases are dried with K$_2$CO$_3$, filtered and evaporated to a few milliliters in vacuo. Addition of CH$_2$Cl$_2$ (250 ml) causes the precipitation of virtually colourless K[C$_2$F$_5$B(OCH$_3$)(CN)$_2$], which is subsequently dried in vacuo. The yield of potassium dicyanomethoxypentafluoroethylborate is 17.7 g (70.2 mmol), 92% based on the potassium trimethoxypentafluoroethylborate employed. Decomposition from 210° C.; Raman spectroscopy: ν (CN)=2210, 2216 cm$^{-1}$. The product is characterized by NMR-spectroscopy:

$^{11}$B{$^1$H}-NMR: δ, ppm=−12.7 t (1B), $^2J_{F,B}$=23.1 Hz.
$^{19}$F{$^1$H}-NMR: δ, ppm=−82.0 s (CF$_3$, 3F); −128.9 q (CF$_2$, 2F), $^2J_{F,B}$=23.3 Hz.
$^1$H{$^{11}$B}-NMR: δ, ppm=3.25 s (OCH$_3$, 3H).
$^{13}$C{$^1$H}-NMR: δ, ppm=53.38 q (OCH$_3$, 1C), $^1J_{H,C}$=139.84 Hz.

EXAMPLE 5

Tetraphenylphosphonium dicyanomethoxytrifluoromethylborate—[(C$_6$H$_5$)$_4$P][CF$_3$B(OCH$_3$)(CN)$_2$]

A.

K[CF$_3$BF$_3$] + 2 (CH$_3$)$_3$SiCN + (CH$_3$)$_3$SiOCH$_3$ +

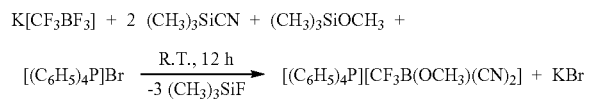

K[CF$_3$BF$_3$] (0.2 g, 1.1 mmol) is weighed out into a cylindrical reaction vessel with a glass valve and PTFE spindle (Young, London) and a magnetic stirrer bar. A mixture of trimethylsilyl cyanide and methoxytrimethylsilane (10 ml, ~10:1 v/v) is condensed onto the salt. The reaction mixture is stirred at room temperature for 12 hours. All volatile constituents are removed in vacuo, and the residue is dissolved in deionized water (15 ml). Slow dropwise addition of a solution of [Ph$_4$P]Br (0.6 g, 1.4 mmol) in deionized water (30 ml) causes the formation of a colourless precipitate, which is filtered off and subsequently dried in vacuo. The yield of tetraphenylphosphonium dicyanomethoxytrifluoromethylborate is 0.5 g (1.1 mmol), 92% based on the potassium trifluorotrifluoromethylborate, K[CF$_3$BF$_3$], employed. Melting point: 160° C.; decomposition from 240° C. Raman spectroscopy: ν (CN)=2203 cm$^{-1}$. The product is characterized by NMR-spectroscopy: $^1$H-NMR: δ, ppm=7.8-7.92 m (4C$_6$H$_5$, 16H); 7.97-8.05 m (4C$_6$H$_5$, 4H).

$^{13}$C{$^1$H}-NMR (Cation): δ, ppm=136.3 s (4C), 135.6 d (8C), J$_{C,P}$=10 Hz, 131.3 d (8C), J$_{C,P}$=13 Hz, 118.9 d (4C), J$_{C,P}$=91 Hz.
$^{11}$B{$^1$H}-NMR: δ, ppm=−13.5 q (1B), $^2J_{F,B}$=33.3 Hz.
$^{19}$F{$^1$H}-NMR: δ, ppm=−71.2 q (CF$_3$, 3F), $^2J_{F,B}$=33.4 Hz.
Elemental analysis: found, %: C, 66.97; H, 4.55; N, 5.37; calculated for C$_{28}$H$_{23}$BF$_3$N$_2$OP: C, 66.96; H, 4.62; N, 5.58.

B.

K[CF$_3$B(OCH$_3$)$_3$] + 2 (CH$_3$)$_3$SiCN +

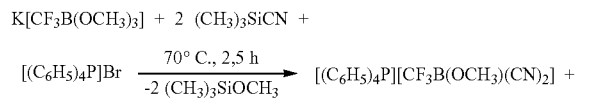

K[CF$_3$B(OCH$_3$)$_3$] (1.1 g, 5.2 mmol) is initially introduced into a cylindrical reaction vessel with a glass valve and PTFE spindle (Young, London) and a magnetic stirrer bar. Trimethylsilyl cyanide (10.0 ml, 74.9 mmol) is condensed in. The reaction mixture is stirred at 70° C. for 2.5 hours. The volatile constituents are then removed in vacuo, and the residue is dissolved in deionized water (20 ml). An aqueous solution of [Ph$_4$P]Br (2.6 g, 6.2 mmol, 200 ml) is added to the solution. The precipitate is filtered off and dried in vacuo. The yield of tetraphenylphosphonium dicyano-methoxytrifluoromethylborate is 2.4 g (4.8 mmol), 96% based on the potassium trimethoxytrifluoromethylborate, K[CF$_3$B(OCH$_3$)$_3$], employed. The NMR spectra of the obtained product are conside with spectra described in the Example 5A.

EXAMPLE 6

Tetra-n-butylammonium dicyanomethoxytrifluoromethylborate—[(C$_4$H$_9$)$_4$N][CF$_3$B(OCH$_3$)(CN)$_2$]

A

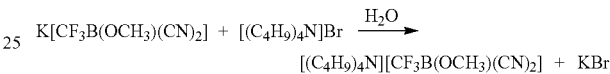

K[CF$_3$B(OCH$_3$)(CN)$_2$] (1.0 g, 4.9 mmol), prepared as described in Example 2, is dissolved in deionized water (20 ml), and [n-Bu$_4$N]Br (2.0 g, 6.2 mmol) in deionized water (40 ml) is added. The fine precipitate is extracted with CH$_2$Cl$_2$ (3×15 ml). The combined organic phases are washed with deionized water (4×2 ml) and dried using MgSO$_4$. After filtration the solvent is removed using a rotary evaporator. The yield of tetra-n-butylammonium dicyanomethoxytrifluoromethylborate is 1.5 g (3.7 mmol), 75% based on the potassium dicyanomethoxytrifluoromethylborate, K[CF$_3$B(OCH$_3$)(CN)$_2$], employed.

Raman spectroscopy: ν (CN)=2203 cm$^{-1}$.
$^1$H-NMR: δ, ppm=1.0 t (4-CH$_3$, 12H), $^3J_{H,H}$=7 Hz; 1.4 m (4-CH$_2$, 8H), $^3J_{H,H}$=7 Hz, 1.7-1.8 m (4-CH$_2$, 8H); 3.3-3.5 m (4-CH$_2$, 8H).
$^{13}$C{$^1$H}-NMR (Cation): δ, ppm=59.3 s (4C), 24.3 s (4C), 20.2 s (4C), 13.7 s (4C).
$^{11}$B{$^1$H}-NMR: δ, ppm=−13.5 q (1B), $^2J_{F,B}$=33.3 Hz.
$^{19}$F{$^1$H}-NMR: δ, ppm=−71.2 q (CF$_3$, 3F), $^2J_{F,B}$=33.4 Hz.
Elemental analysis: found, %: C, 59.13; H, 9.68; N, 10.21; calculated for C$_{20}$H$_{39}$BF$_3$N$_3$O: C, 59.26; H, 9.70; N, 10.37.

B

K[CF$_3$B(OCH$_3$)$_3$] + 2 (CH$_3$)$_3$SiCN +

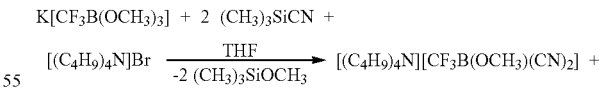

Potassium trimethoxytrifluoromethylborate K[CF$_3$B(OCH$_3$)$_3$] (1.0 g, 4.71 mmol), placed into 10 mL reaction vessel with a glass valve and PTFE spindle (Young, London) and a magnetic stirrer bar, is dissolved in 4 mL of THF. The trimethylsilyl cyanide (1.9 ml, 14.2 mmol) is added to this solution and the reaction mixture is stirred at room temperature for 18 hours. All volatile products are removed in vacuo and the residue is dissolved in 2 mL of deionized water. Tetrabutylammonium bromide (C$_4$H$_9$)$_4$NBr (1.8 g, 5.65 mmol) dissolved in 2 mL of deionized water is added by the mixing of the reaction mixture with magnetic stirring bar. The reaction mixture is left stirring of the next 15 min and the ionic liquid is separated and washed two times with deionized water (1 mL). After drying in vacuo 1.2 g (2.96 mmol) of tetra-n-butylammonium dicyanomethoxytrifluoromethylborate [(C$_4$H$_9$)$_4$N][CF$_3$B(OCH$_3$)(CN)$_2$] is obtained. The yield is 63% based on the potassium trimethoxytrifluoromethylborate, K[CF$_3$B(OCH$_3$)$_3$], employed. The NMR spectra of the obtained product are conside with the spectra described in the Example 6A.

EXAMPLE 7

1-Ethyl-3-methylimidazolium dicyanomethoxytrifluoromethylborate—[C$_6$H$_{11}$N$_2$][CF$_3$B(OCH$_3$)(CN)$_2$]

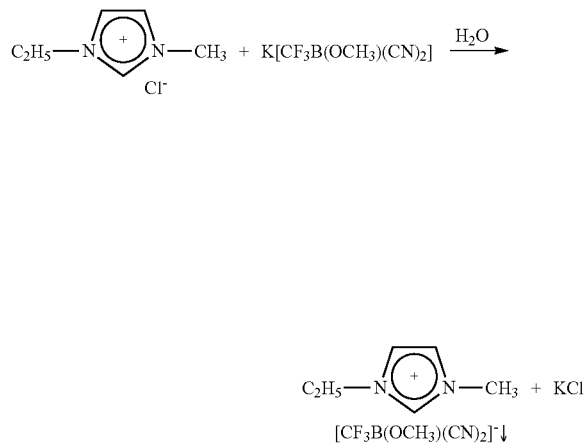

K[CF$_3$B(OCH$_3$)(CN)$_2$] (5.5 g, 27.2 mmol), prepared as described in Example 2, is dissolved in deionized water (10 ml), and 1-ethyl-3-methylimidazolium chloride [EMIM]Cl (4.1 g, 27.9 mmol), dissolved in deionized water (10 ml), is added by the mixing of the reaction mixture with the magnetic stirring bar. The ionic liquid is separated, washed with deionized water (4×2 ml) and dried in vacuo at 60° C. The yield of liquid 1-Ethyl-3-methylimidazolium dicyanomethoxytrifluoromethylborate is 3.7 g (13.5 mmol), 49% based on the potassium dicyanomethoxytrifluoromethyl-borate, K[CF$_3$B(OCH$_3$)(CN)$_2$], employed. The product is analyzed by ion chromatography and showed the low content of impurities on halides; chloride: 104 ppm, fluoride: 41 ppm.

Water content (Karl-Fischer Titration) is 58 ppm.

Raman spectroscopy: v (CN)=2205 cm$^{-1}$ $^1$H{$^{11}$B}-NMR: δ, ppm=8.95 d, d (CH, 1H), $^4J_{H,H}$=1.7 Hz; 7.71 d, d (CH, 1H), $^3J_{H,H}$=$^4J_{H,H}$=1.7 Hz; 7.61 d, d (CH, 1H) $^3J_{H,H}$=$^4J_{H,H}$=1.6 Hz; 4.39 t (CH$_2$, 2H), J$_{H,H}$=7.36 Hz; 4.07 s (CH$_3$, 3H); 3.20 s (OCH$_3$, 3H); 1.50 t (CH$_3$, 3H), J$_{H,H}$=7.40 Hz $^{13}$C{$^1$H}-NMR: δ, ppm=136.28 s (CH, 1C); 125.01 s (CH, 1C); 122.28 s (CH, 1C); 53.15 s (OCH$_3$, 1C); 45.52 s (CH$_2$, 1C); 36.40 s (CH$_3$, 1C); 15.28 (CH$_3$, 1C)

$^{11}$B{$^1$H}-NMR: δ, ppm=−13.5 q (1B), $^2J_{F,B}$=33.3 Hz.

$^{19}$F{$^1$H}-NMR: δ, ppm=−71.2 q (CF$_3$, 3F), $^2J_{F,B}$=33.4 Hz.

Elemental analysis: found, %: C, 43.77; H, 5.28; N, 20.59; calculated for C$_{10}$H$_{14}$BF$_3$N$_4$O: C, 43.83; H, 5.15; N, 20.44.

EXAMPLE 8

N-Butyl-N-methylpyrrolidinium dicyanomethoxytrifluoromethylborate—[C$_9$H$_{20}$N][CF$_3$B(OCH$_3$)(CN)$_2$]

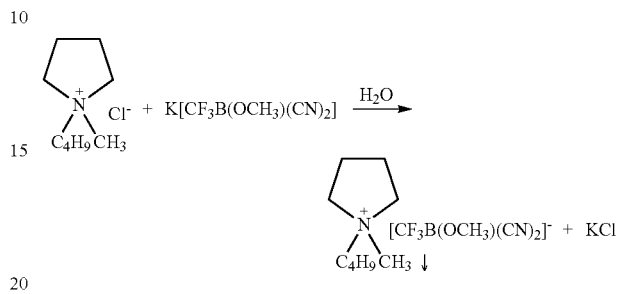

K[CF$_3$B(OCH$_3$)(CN)$_2$] (250 mg, 1.2 mmol), prepared as described in Example 2, is dissolved in deionized water (10 ml), and 1-butyl-1-methylpyrrolidinium chloride (300 mg, 1.7 mmol), dissolved in deionized water (20 ml), is added. The ionic liquid is extracted with CH$_2$Cl$_2$ (3×10 ml). The combined organic phases are washed with deionized water (4×2 ml) and dried using MgSO$_4$. After filtration the CH$_2$Cl$_2$ is removed using a rotary evaporator. The yield of liquid N-butyl-N-methylpyrrolidinium dicyanomethoxytrifluoromethylborate is 140 mg (0.46 mmol), 38% based on the potassium dicyanomethoxytrifluoromethyl-borate, K[CF$_3$B(OCH$_3$)(CN)$_2$], employed.

Raman spectroscopy: v (CN)=2203 cm$^{-1}$.

$^1$H{$^{11}$B}-NMR: δ, ppm=3.67 m (2CH$_2$, 4H); 3.50 m (CH$_2$, 2H); 3.27 s (OCH$_3$, 3H); 3.21 s (CH$_3$, 3H); 2.30 m (2CH$_2$, 4H); 1.88 m (CH$_2$, 2H); 1.44 m (CH$_2$, 2H); 0.98 t (CH$_3$, 3H), $^3J_{H,H}$=7.37 Hz $^{13}$C{$^1$H}-NMR: δ, ppm=65.20 s (CH$_2$, 2C); 65.00 s (CH$_2$, 1C); 53.15 s (OCH$_3$, 1C); 48.98 s (CH$_3$, 1C); 26.17 s (CH$_2$, 1C); 22.23 s (CH$_2$, 2C); 20.30 (CH$_2$, 1C); 13.64 s (CH$_3$, 1C).

$^{11}$B{$^1$H}-NMR: δ, ppm=−13.5 q (1B), $^2J_{F,B}$=33.3 Hz.

$^{19}$F{$^1$H}-NMR: δ, ppm=−71.2 q (CF$_3$, 3F), $^2J_{F,B}$=33.4 Hz.

EXAMPLE 9

Tetraphenylphosphonium dicyanomethoxypentafluoroethylborate—[(C$_6$H$_5$)$_4$P][C$_2$F$_5$B(OCH$_3$)(CN)$_2$]

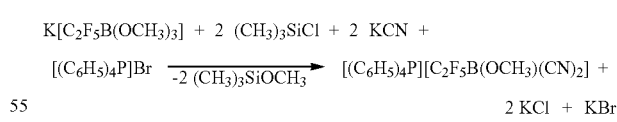

KCN (3.0 g, 46.1 mmol) and KI (0.6 g, 3.9 mmol) are dried for 4 hours at 115° C. in vacuo in a cylindrical reaction vessel with a glass valve and PTFE spindle (Young, London) and a magnetic stirrer bar. Trimethylsilyl chloride (3.0 ml, 2.6 g, 23.6 mmol) is subsequently added, and the reaction mixture is stirred at 100° C. for 3 days. K[C$_2$F$_5$B(OCH$_3$)$_3$] (200 mg, 0.76 mmol) is added in a counterstream of argon, and the mixture is stirred at room temperature for 3 days. The reaction mixture is taken up in 30% H$_2$O$_2$ (20 ml) and stirred for 2 hours. [Ph$_4$P]Br (500 mg, 1.2 mmol) is subsequently dissolved in deionized water (50 ml) and slowly added dropwise to the reaction mixture. The precipitate is filtered off, dried and extracted with acetone (20 ml). The combined acetone phases are evaporated to dryness. The yield of tetraphenylphosphonium dicyanomethoxypentafluoroethylborate is 250 mg (0.45 mmol), 60% based on the potassium trimethoxypentafluoroethylborate, $K[C_2F_5B(OCH_3)_3]$, employed. Melting point: 155° C.; decomposition from 280° C.

Raman spectroscopy: $\nu$ (CN)=2206 cm$^{-1}$.

$^1$H-NMR: $\delta$, ppm=7.8-7.92 m (4C$_6$H$_5$, 16H); 7.97-8.05 m (4C$_6$H$_5$, 4H).

$^{13}$C{$^1$H}-NMR (Cation): $\delta$, ppm=136.3 s (4C), 135.6 d (8C), $J_{C,P}$=10 Hz, 131.3 d (8C), $J_{C,P}$=13 Hz, 118.9 d (4C), $J_{C,P}$=91 Hz.

$^{11}$B{$^1$H}-NMR: $\delta$, ppm=−12.7 t (1B), $^2J_{F,B}$=23.1 Hz.

$^{19}$F{$^1$H}-NMR: $\delta$, ppm=−82.0 s (CF$_3$, 3F); −128.9 q (CF$_2$, 2F), $^2J_{F,B}$=23.3 Hz.

EXAMPLE 10

N-Butyl-N-methylpyrrolidinium dicyanomethoxypentafluoroethylborate—$[C_9H_{20}N][C_2F_5B(OCH_3)(CN)_2]$

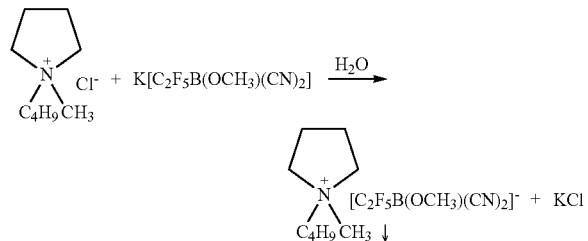

Potassium dicyanomethoxypentafluoroethylborate, $K[C_2F_5B(OCH_3)(CN)_2]$ (6.0 g, 23.8 mmol), prepared as described in Example 4, is dissolved in deionized water (2 ml), and the solution of 1-butyl-1-methylpyrrolidinium chloride [BMPL]Cl (4.7 g, 26.4 mmol) in 2 ml of deionized water is added by the mixing of the reaction mixture with the magnetic stirring bar. The ionic liquid is separated, washed with deionized water (4×2 ml) and dried in vacuo at 50° C. The yield of liquid N-butyl-N-methylpyrrolidinium dicyanomethoxypentafluoroethylborate is 7.9 g (22.2 mmol), 93% based on the potassium dicyanomethoxypentafluoroethylborate, $K[C_2F_5B(OCH_3)(CN)_2]$, employed. The product is analyzed by ion chromatography and showed the low content of impurities on halides; chloride: <5 ppm, fluoride: 8 ppm. Water content (Karl-Fischer Titration) is 130 ppm. Dynamic viscosity (20° C.) is 78.3 mPa·s.

Raman spectroscopy: $\nu$ (CN)=2202 cm$^{-1}$ $^{11}$B{$^1$H}-NMR: $\delta$, ppm=−12.7 t (1B), $^2J_{F,B}$=23.1 Hz.

$^{19}$F{$^1$H}-NMR: $\delta$, ppm=−82.0 s (CF$_3$, 3F); −128.9 q (CF$_2$, 2F), $^2J_{F,B}$=23.3 Hz.

$^1$H{$^{11}$B}-NMR: $\delta$, ppm=3.67 m (2CH$_2$, 4H); 3.50 m (CH$_2$, 2H); 3.27 s (OCH$_3$, 3H); 3.21 s (CH$_3$, 3H); 2.30 m (2CH$_2$, 4H); 1.88 m (CH$_2$, 2H); 1.44 m (CH$_2$, 2H); 0.98 t (CH$_3$, 3H), $^3J_{H,H}$=7.37 Hz $^{13}$C{$^1$H}-NMR: $\delta$, ppm=65.20 s (CH$_2$, 2C); 65.00 s (CH$_2$, 1C); 53.39 s (OCH$_3$, 1C); 48.98 s (CH$_3$, 1C); 26.17 s (CH$_2$, 1C); 22.23 s (CH$_2$, 2C); 20.30 (CH$_2$, 1C); 13.64 s (CH$_3$, 1C).

Elemental analysis: found, %: C, 47.47; H, 6.44; N, 11.77; calculated for $C_{14}H_{23}BF_5N_3O$: C, 47.35; H, 6.53; N, 11.83.

EXAMPLE 11

1-Ethyl-3-methylimidazolium dicyanomethoxypentafluoroethylborate—$[C_6H_{11}N_2][C_2F_5B(OCH_3)(CN)_2]$

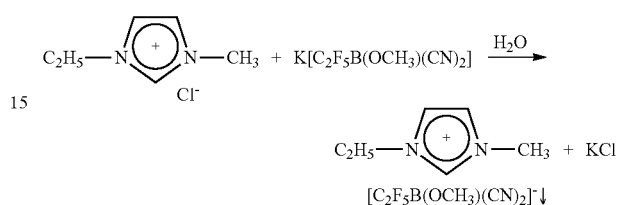

$K[C_2F_5B(OCH_3)(CN)_2]$ (5.2 g, 20.6 mmol), prepared as described in Example 4, is dissolved in deionized water (10 ml), and 1-ethyl-3-methylimidazolium chloride [EMIM]Cl (3.5 g, 23.9 mmol), dissolved in deionized water (10 ml), is added by the mixing of the reaction mixture with the magnetic stirring bar. The ionic liquid is separated, washed with deionized water (4×2 ml) and dried in vacuo at 60° C. The yield of liquid 1-Ethyl-3-methylimidazolium dicyanomethoxypentafluoroethylborate is 4.0 g (12.3 mmol), 59% based on the potassium dicyanomethoxypentafluoroethylborate, $K[C_2F_5B(OCH_3)(CN)_2]$, employed. The product is analyzed by ion chromatography and showed the low content of impurities on halides; chloride: 20 ppm, fluoride: 5 ppm. Water content (Karl-Fischer Titration) is 27 ppm.

Raman: $\nu$ (CN)=2204 cm$^{-1}$.

$^1$H{$^{11}$B}-NMR: $\delta$, ppm=8.90 d, d (CH, 1H), $^4J_{H,H}$≈1.8 Hz; 7.70 d, d (CH, 1H), $^3J_{H,H}$≈$^4J_{H,H}$≈1.7 Hz; 7.63 d, d (CH, 1H) $^3J_{H,H}$≈$^4J_{H,H}$≈1.7 Hz; 4.39 t (CH$_2$, 2H), $J_{H,H}$=7.36 Hz; 4.06 s (CH$_3$, 3H); 3.25 s (OCH$_3$, 3H); 1.50 t (CH$_3$, 3H), $J_{H,H}$=7.41 Hz.

$^{13}$C{$^1$H}-NMR: $\delta$, ppm=136.78 s (CH, 1C); 125.07 s (CH, 1C); 122.38 s (CH, 1C); 53.15 s (OCH$_3$, 1C); 45.61 s (CH$_2$, 1C); 36.46 s (CH$_3$, 1C); 15.34 s (CH$_3$, 1C).

$^{11}$B{$^1$H}-NMR: $\delta$, ppm=−12.7 t (1B), $^2J_{F,B}$=23.1 Hz.

$^{19}$F{$^1$H}-NMR: $\delta$, ppm=−82.0 s (CF$_3$, 3F); −128.9 q (CF$_2$, 2F), $^2J_{F,B}$=23.3 Hz.

Elemental analysis: found, %: C, 40.83; H, 4.52; N, 17.54; calculated for $C_{11}H_{14}BF_5N_4O$: C, 40.77; H, 4.35; N, 17.29.

EXAMPLE 12

1-Butyl-3-methylimidazolium dicyanomethoxypentafluoroethylborate—$[C_8H_{15}N_2][C_2F_5B(OCH_3)(CN)_2]$

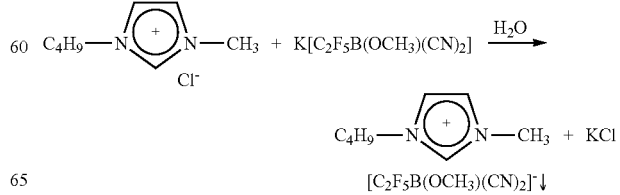

Potassium dicyanomethoxypentafluoroethylborate, $K[C_2F_5B(OCH_3)(CN)_2]$ (500 mg, 1.9 mmol), prepared as described in Example 4, is dissolved in deionized water (10 ml), and 1-butyl-3-methylimidazolium chloride, [BMIM]Cl (450 mg, 2.6 mmol), dissolved in deionized water (10 ml), is added by the mixing of the reaction mixture with the magnetic stirring bar. The ionic liquid is extracted with $CH_2Cl_2$ (2×10 ml). The combined organic phases are washed with deionized water (4×2 ml) and dried using $MgSO_4$. After filtration the $CH_2Cl_2$ is removed using a rotary evaporator. The yield of liquid 1-butyl-3-methylimidazolium dicyanomethoxypentafluoroethylborate is 530 mg (1.5 mmol), 79% based on the potassium dicyanomethoxypentafluoroethylborate, $K[C_2F_5B(OCH_3)(CN)_2]$, employed.

Raman spectroscopy: $v$ (CN)=2204 $cm^{-1}$.

$^1$H-NMR: δ, ppm=8.95 d, d (CH, 1H) $^4J_{H,H}\approx1.6$ Hz; 7.69 d, d (CH, 1H), $^3J_{H,H}\approx^4J_{H,H}=1.7$ Hz; 7.65 d, d (CH, 1H) $^3J_{H,H}\approx^4J_{H,H}\approx1.7$ Hz; 4.34 t ($CH_2$, 2H), $J_{H,H}=7.33$ Hz; 4.02 s ($CH_3$, 3H); 3.25 s ($OCH_3$, 3H); 1.92 m ($CH_2$, 2H); 1.39 m ($CH_2$, 2H); 0.92 t ($CH_3$, 3H), $J_{H,H}=7.37$ Hz.

$^{13}C\{^1H\}$-NMR (Kation): δ, ppm=137.40 s (CH, 1C); 124.86 s (CH, 1C); 123.47 s (CH, 1C); 53.20 s ($OCH_3$, 1C); 50.30 s ($CH_2$, 1C); 36.68 s ($CH_3$, 1C); 32.59 s ($CH_2$, 1C); 19.98 s ($CH_2$, 1C); 13.50 s ($CH_3$, 1C).

$^{11}B\{^1H\}$-NMR: δ, ppm=−12.7 t (1B), $^2J_{F,B}=23.1$ Hz.

$^{19}F\{^1H\}$-NMR: δ, ppm=−82.0 s ($CF_3$, 3F); −128.9 q ($CF_2$, 2F), $^2J_{F,B}=23.3$ Hz.

EXAMPLE 13

Diethylmethylsulfonium dicyanomethoxypentafluoroethylborate—$[C_5H_{13}S][C_2F_5B(OCH_3)(CN)_2]$

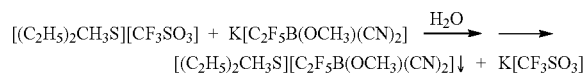

$[(C_2H_5)_2CH_3S][CF_3SO_3]$ + $K[C_2F_5B(OCH_3)(CN)_2]$ $\xrightarrow{H_2O}$ $[(C_2H_5)_2CH_3S][C_2F_5B(OCH_3)(CN)_2]\downarrow$ + $K[CF_3SO_3]$ Potassium dicyanomethoxypentafluoroethylborate, $K[C_2F_5B(OCH_3)(CN)_2]$ (8.0 g, 31.7 mmol), prepared as described in Example 4, is dissolved in deionized water (30 ml), and diethylmethylsulfonium trifluoromethansulfonat (6.7 g, 26.3 mmol), dissolved in deionized water (30 ml), is added by the mixing of the reaction mixture with the magnetic stirring bar. The ionic liquid is extracted with $CH_2Cl_2$ (10×15 ml). The combined organic phases are are washed with deionized water (5×10 ml) and dried using $MgSO_4$. After filtration the $CH_2Cl_2$ is removed using a rotary evaporator. The yield of liquid Diethylmethylsulfonium dicyanomethoxypentafluoroethylborate is 8.0 g (25.1 mmol), 95% based on the diethylmethylsulfonium trifluoromethansulfonat employed. The product is analyzed by ion chromatography and showed the low content of impurities on halides; chloride: 8 ppm, fluoride: 10 ppm. Water content (Karl-Fischer Titration) is 163 ppm. Dynamic viscosity (20° C.) is 43.2 mPa·s.

Raman: $v$ (CN)=2203 $cm^{-1}$ $^1H\{^{11}B\}$-NMR: δ, ppm=3.48 m (2$CH_2$, 4H); 3.26 s ($OCH_3$, 3H); 3.02 s ($CH_3$, 3H); 1.52 t (2$CH_3$, 6H), $^3J_{H,H}=7.44$ Hz.

$^{13}C\{^1H\}$-NMR: δ, ppm=53.37 s ($OCH_3$, 1C); 35.98 s (2$CH_2$, 2C); 21.42 s ($CH_3$, 1C); 8.75 s (2$CH_3$, 2C).

$^{11}B\{^1H\}$-NMR: δ, ppm=−12.7 t (1B), $^2J_{F,B}=23.1$ Hz.

$^{19}F\{^1H\}$-NMR: δ, ppm=−82.0 s ($CF_3$, 3F); −128.9 q ($CF_2$, 2F), $^2J_{F,B}=23.3$ Hz.

Elemental analysis: found, %: C, 37.62; H, 4.90; S, 8.75; calculated for $C_{10}H_{16}BF_5N_2OS$: C, 37.76; H, 5.07; S, 10.08.

EXAMPLE 14

Lithium dicyanomethoxypentafluoroethylborate—$Li[C_2F_5B(OCH_3)(CN)_2]$

To the solution of Potassium dicyanomethoxypentafluoroethylborate, $K[C_2F_5B(OCH_3)(CN)_2]$ (1.0 g, 3.9 mmol), prepared as described in Example 4, in 3 ml of acetonitrile the solution Lithiumtetrafluoroborat in acetonitrile (0.95 M, 4.1 ml, 3.9 mmol $LiBF_4$) is added by mixing the reaction mixture with the magnetic stirring bar. The suspension is cooled down to 0° C. and filtrate. The precipitant ($KBF_4$) is washed with cold acetonitrile (0° C.; 3 ml) and dried in vacuo. The filtrate is evaporated in vacuo and the residue is dried in vacuo for 20 hours at 50° C.

The yield of potassium tetrafluoroborate $KBF_4$ 0.49 g (3.91 mmol), 99% from the theoretical yield.

The yield of Lithium dicyanomethoxypentafluoroethylborate is quantitative.

The product is characterised by means NMR-spectroscopy.

$^{11}B\{^1H\}$-NMR: δ, ppm=−12.7 t (1B), $^2J_{F,B}=23.1$ Hz.

$^{19}F\{^1H\}$-NMR: δ, ppm=−82.0 s ($CF_3$, 3F); −128.9 q ($CF_2$, 2F), $^2J_{F,B}=23.3$ Hz.

EXAMPLE 15

Kaliumdicyanoethoxytrifluoromethylborate—$K[CF_3B(OEt)(CN)_2]$ $K[CF_3BF_3]$ (0.8 g, 4.5 mmol) and a mixture of trimethylsilylcyanide (TMSCN) with ethoxytrimethylsilane (TMSOEt) (~20 mL, TMSCN/TMSOEt, ~122/28 mmol) are stirred at 50° C. for 24 hours. All volatile compounds are distilled off and the residue is dissolved in acetone. By addition of $CH_2Cl_2$ the solid material is precipitated. After filtration and drying in vacuum 0.9 g of $K[CF_3B(OEt)(CN)_2]$ is isolated. The yield is 92% calculating on the $K[CF_3BF_3]$ employed. The product is characterised by means NMR-spectroscopy.

$^{11}B\{^1H\}$-NMR: δ, ppm=−14.58 q (1B), $^2J_{F,B}=32.9$ Hz.

$^1H\{^{11}B\}$-NMR: δ, ppm=3.52 q ($OCH_2$, 2H), $^3J_{H,H}=7.0$ Hz; 1.10 t ($CH_3$, 3H).

$^3J_{H,H}=7.0$ Hz.

EXAMPLE A

Formulations and Device

The following electrolyte formulations are synthesized to demonstrate the advantage of electrolyte formulations according to the invention relative to electrolyte formulations of the prior art containing the tetracyanoborate anion if the same cation is used.

EXAMPLE A-1

1. Electrolyte Preparation

The ionic liquids used for electrolyte preparation are summarized in Table 1.

TABLE 1

The ionic liquids in this study

| | cation | anion | abbreviation |
|---|---|---|---|
| 1 | 1-ethyl-3-methylimidazolium 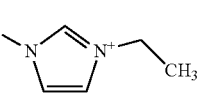 | Tetracyanoborate 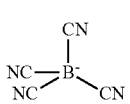 | EMIM TCB |
| 2 | 1-ethyl-3-methylimidazolium 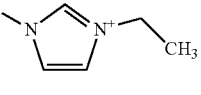 | Pentafluoroethyldicyano methoxyfluoroborate 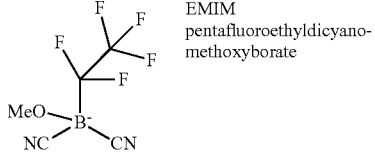 | EMIM pentafluoroethyldicyano-methoxyborate |

The electrolyte mixtures employed in table 2 are prepared with 1,3-dimethylimidazolium iodide (mmim I), 1-ethyl-3-methylimidazolium iodide (emim I), elemental iodine, N-butylbenzimidazole, guanidinium thiocyanate and the ionic liquids listed in the previous table in the molar ratio of 36:36:5:10:2:48.

The compounds mmim I, emim I, $I_2$, N-butylbenzimidazole and guanidinium thiocyanate are commercially available or are synthesized according to known literature such as Bonhote, P. et al Inorg. Chem. 1996, 35, 1168-1178.

2: The Fabrication of the Dye Sensitized Solar Cell (DSSC)

The dye sensitized solar cells are fabricated as disclosed in U.S. Pat. No. 5,728,487 or WO 2007/093961:

A double-layer, mesoporous $TiO_2$ electrode was prepared as disclosed in Wang P et al., J. Phys. Chem. B 2003, 107, 14336, in particular page 14337, in order to obtain a photoanode consisting of a double layer structure. To prepare a transparent nanoporous $TiO_2$ electrode, a screen printing paste containing terpineol solvent and nanoparticulate $TiO_2$ of anatase phase with 20 nm diameter was deposited on a transparent conductive substrate to 5 mm×5 mm squared shape by using a hand printer. The paste was dried for 10 minutes at 120 degrees Celsius. Another screen printing paste containing $TiO_2$ with 400 nm diameter was then deposited on top of the nanoporous layer to prepare an opaque layer. The double layer film was then sintered at 500 degrees Celsius for an hour with the result of an underlying transparent layer (7 microns thick) and a top opaque layer (4 microns thick). After sintering, the electrode was immersed in 40 mM aqueous solution of $TiCl_4$ (Merck) for 30 minutes at 70 degrees Celsius and then rinsed with pure water sufficiently. Thus $TiCl_4$-treated electrode was dried at 500 degrees Celsius for 30 minutes just before dye sensitization. The electrode was dipped into a 0.3 mM Z907 dye solution of acetonitrile (Merck HPLC grade) and tert-butyl alcohol (Merck), v:v=1:1 for 60 hours at 19 degrees Celsius. The counter electrode was prepared with thermal pyrolysis method as disclosed in the reference above. A droplet of 5 mM solution of platinic acid (Merck) was casted at 8 μl/cm2 and dried on a conductive substrate. The dye sensitized solar cell was assembled by using 30 micron thick Bynel (DuPont, USA) hot-melt film to seal up by heating. The internal space was filled with each of the electrolyte formulations as described above to produce the corresponding devices.

The dye Z907 is an amphiphilic ruthenium sensitizer Ru(2,2'-bipyridine 4,4'-dicarboxylic acid) (4,4'-dinonyl-2,2'-bipyridine)$(NCS)_2$ or [Ru(H2dcbpy)(dnbpy)$(NCS)_2$].

The measurements of photocurrent-voltage curves were carried out under Air Mass 1.5 simulated sunlight with temperature control.

3. The DSSC Characteristics at Varied Temperature

The measurements of photocurrent-voltage curves were carried out under Air Mass 1.5 simulated sunlight with temperature control at 25° C. and 12° C. with photomask of 4×4 cm². Characteristic photovoltaic parameters were summarized in table 2. Especially at lower temperature, examined DSSC containing electrolyte 2 with perfluoroethylcyano methoxyfluoroborate salt showed superior performance owing to its higher photocurrent and fill factor maintained at low temperature.

Electrolyte 1 comprising emim TCB.

Electrolyte 2 comprising emim pentafluoroethyldicyanomethoxyborate Table 2 shows detailed photovoltaic parameters of the devices made according to example A represented by the short-circuit photocurrent density ($J_{SC}$), the open-circuit photovoltage ($V_{OC}$), the fill factor (FF), the photovoltaic conversion efficiency (η) and the Nernst diffusion resistance obtained from FIGS. 1 and 2.

| Electrolyte | $J_{SC}$ [mAcm$^{-2}$] | $V_{OC}$ [V] | FF | η [%] | $Z_{ND}$ [Ω] |
|---|---|---|---|---|---|
| 1* (25° C.) | 11.36 | 0.677 | 0.618 | 4.75 | 31 |
| 1* (12° C.) | 10.09 | 0.708 | 0.494 | 3.53 | 48 |
| 2  (25° C.) | 11.08 | 0.671 | 0.650 | 4.83 | 27 |
| 2  (12° C.) | 9.45 | 0.696 | 0.571 | 3.78 | 38 |

*not according to the invention

The impedance spectrum of the photovoltaic device comprising Electrolyte 1 at 25° C. and 12° C. is given in FIG. 1 and the impedance spectrum of the photovoltaic device comprising Electrolyte 2 at 25° C. and 12° C. are given in FIG. 2.

EXAMPLE A-2

1. Electrolyte Preparation

The ionic liquids used in this invention report are summarized in Table 3.

TABLE 3

The ionic liquids in this study

| | cation | anion |
|---|---|---|
| 1 | 1-ethyl-3-methylimidazolium | Tetracyanoborate = TCB |
| 3 | emim | [B(CF$_3$)(OCH$_3$)(CN)$_2$] |
| 4' | 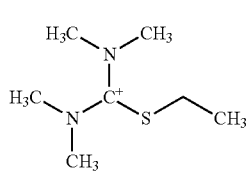 | emim [B(CF$_3$)(OCH$_3$)(CN)$_2$] |
| 5' | 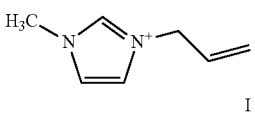 | emim [B(CF$_3$)(OCH$_3$)(CN)$_2$] |
| 6' | 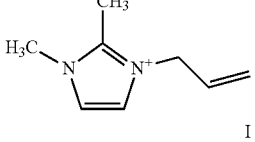 | emim [B(CF$_3$)(OCH$_3$)(CN)$_2$] |
| 7' | 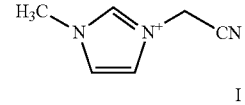 | emim [B(CF$_3$)(OCH$_3$)(CN)$_2$] |
| 8' | 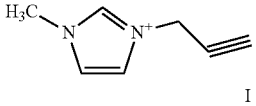 | emim [B(CF$_3$)(OCH$_3$)(CN)$_2$] |
| 9' | 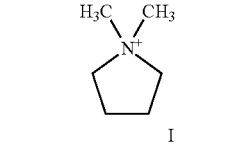 | emim [B(CF$_3$)(OCH$_3$)(CN)$_2$] |
| 10' |  | emim [B(CF$_3$)(OCH$_3$)(CN)$_2$] |

'used as a mixture

The electrolyte formulations are prepared analogously as disclosed in A-1 with the given molar ratio and the compounds as indicated below. The fabrication of the devices were done as described above—however the results are lower than expected which can be seen from the comparison data for emimTCB which merely shows an efficiency of 4.1% of electrolyte formulation 1 (see former data 4.75%) and formulation 1-1 which is below all measurements done so far—which means this study of ionic liquids needs to be interpreted in the light of this comparison to TCB.

Electrolyte formulation 1-1* given in molar ratio: 60 emimI, 5 I$_2$, 60 emimTCB, 2 guaSCN, 10 NBB;

Electrolyte formulation 3 given in molar ratio: 60 emimI, 5 I$_2$, 60 emim[B(CF$_3$)(OCH$_3$)(CN)$_2$], 2 guaSCN, 10 NBB;

Electrolyte formulation 4 given in molar ratio: 60 S-ethyl-N,N,N'N'-tetramethylisothiouroniumI, 5 I$_2$, 60 emim[B(CF$_3$)(OCH$_3$)(CN)$_2$], 2 guaSCN, 10 NBB;

Electrolyte formulation 5 given in molar ratio: 60 1-allyl-3-methylimidazoliumI, 5 I$_2$, 60 emim[B(CF$_3$)(OCH$_3$)(CN)$_2$], 2 guaSCN, 10 NBB;

Electrolyte formulation 6 given in molar ratio: 60 1-allyl-2,3-dimethylimidazoliumI, 5 I$_2$, 60 emim[B(CF$_3$)(OCH$_3$)(CN)$_2$], 2 guaSCN, 10 NBB;

Electrolyte formulation 7 given in molar ratio: 60 1-cyanomethyl-3-methylimidazoliumI, 5 I$_2$, 60 emim[B(CF$_3$)(OCH$_3$)(CN)$_2$], 2 guaSCN, 10 NBB;

Electrolyte formulation 8 given in molar ratio: 60 1-methyl-3-propinylimidazoliumI, 5 I$_2$, 60 emim[B(CF$_3$)(OCH$_3$)(CN)$_2$], 2 guaSCN, 10 NBB;

Electrolyte formulation 9 given in molar ratio: 60 1,1-dimethylpyrrolidiniumI, 5 I$_2$, 60 emim[B(CF$_3$)(OCH$_3$)(CN)$_2$], 2 guaSCN, 10 NBB;

Electrolyte formulation 10 given in molar ratio: 60 trimethylsulfoniumI, 5 I$_2$, 60 emim[B(CF$_3$)(OCH$_3$)(CN)$_2$], 2 guaSCN, 10 NBB.

TABLE 4

Electrolyte formulations employed in the present invention for devices fabricated as described before.

| Electrolyte formulation | DSC efficiency at 25° C. under AM1.5 |
|---|---|
| 1* | 4.1% ± 0.1% |
| 1-1* | 4.1% ± 0.1% |
| 3 | 3.6 ± 0.2% |
| 4 | 2.1 ± 0.1% |
| 5 | 3.2 ± 0.1% |
| 6 | 2.0 ± 0.1% |
| 7 | 1.1 ± 0.3% |
| 8 | 0.1 ± 0.1% |
| 9 | 1.5 ± 0.1% |
| 10 | 0.8 ± 0.6% |

*not according to the invention

EXAMPLE B

The following electrolyte formulations are synthesized according to example

A and used as electrolytes in DSSC test cells as prepared according to example A:

Electrolyte formulation 11 given in molar ratio: 36 mmimI, 36 emimI, 5 I$_2$, 72 bmpITCB, 2 guaSCN, 10 NBB;

Electrolyte formulation 12 given in molar ratio: 36 mmimI, 36 emimI, 5 I$_2$, 72 bmpI[B(C$_2$F$_5$)(OMe)(CN)$_2$], 2 guaSCN, 10 NBB;

Electrolyte formulation 13 given in molar ratio: 36 mmimI, 36 emimI, 5 I$_2$, 72 diethylmethylsulfonium [B(C$_2$F$_5$)(OMe)(CN)$_2$], 2 guaSCN, 10 NBB.

TABLE 5 summarizes the results of the measurements of
the above cited electrolyte formulations according to
example 4: η = DSC efficiency

| Electrolyte | $J_{SC}$[mAcm$^{-2}$] | $V_{OC}$ [V] | FF | η[%] |
|---|---|---|---|---|
| 11* | 8.18 | 0.70 | 0.58 | 3.47 |
| 11* | 8.55 | 0.75 | 0.55 | 3.48 |
| 12 | 7.75 | 0.72 | 0.62 | 3.72 |
| 12 | 8.03 | 0.67 | 0.61 | 3.77 |
| 13 | 8.20 | 0.73 | 0.69 | 4.09 |
| 13 | 8.35 | 0.71 | 0.69 | 4.11 |

*not according to the invention

Figure 1:
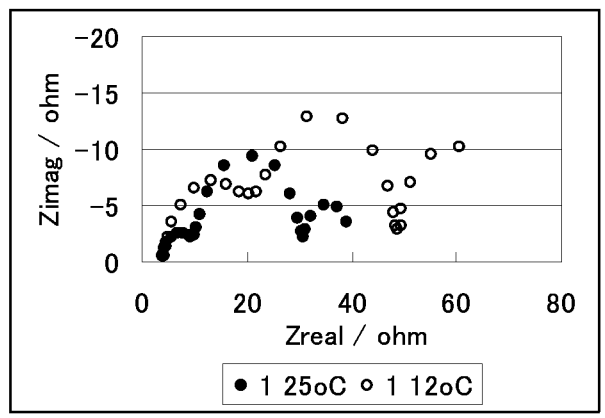
FIG. 1 gives the impedance spectrum of device 1 containing electrolyte formulation 1 at 25° C. and 12° C.
Figure 2:
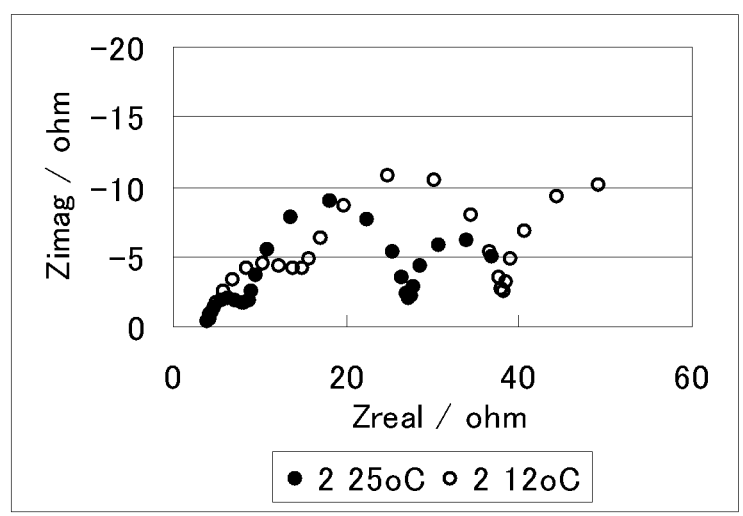
FIG. 2 gives the impedance spectrum of device 2 containing electrolyte formulation 2 at 25° C. and 12° C.

The invention claimed is:

1. A compound containing a borate anion of formula Ia $$[B(R_f)(CN)_x(OR^*)_{3-x-y}(F)_y]^- \qquad \text{Ia}$$

in which
x is 1 or 2,
y is 0 or 1,
x+y is <3,
$R_f$ is a straight-chain or branched perfluoroalkyl group having 1 to 4 C atoms, $C_6F_5$, $C_6H_5$, partially fluorinated phenyl or phenyl which is monosubstituted or disubstituted by perfluoroalkyl groups having 1 to 4 C atoms, and
$R^*$ is a straight-chain or branched alkyl group having 1 to 4 C atoms.

2. A compound according to claim 1, wherein said compound is of formula (I)

$$[Kt]^{z+}z[B(R_f)(CN)_x(OR^*)_{3-x-y}(F)_y]^- \qquad \text{I}$$

in which
$[Kt]^{z+}$ denotes an inorganic or organic cation or $H^+$,
z is 1 or 2, and
x, y, $R_f$ and $R^*$ have the meaning indicated in claim 1.

3. A compound according to claim 2, wherein $[Kt]^{z+}$ is an organic cation selected from sulfonium, oxonium, ammonium, phosphonium, uronium, thiouronium, guanidinium and heterocyclic cations.

4. A compound according to claim 2, wherein
$[Kt]^{z+}$ is a sulfonium cation of formula $[(R^o)_3S]^+$ (1) or an oxonium cation of formula $[(R^o)_3O]^+$ (2),
$R^o$ is a straight-chain or branched alkyl group having 1-8 C atoms, $R'''_2N-$, nonsubstituted phenyl, or phenyl which is substituted by $R'''$, $OR'''$, $N(R''')_2$, CN or halogen, and
$R'''$ is independently of each other H or straight-chain or branched $C_1$ to $C_8$ alkyl.

5. A compound according to claim 2, wherein
(a) $[Kt]^{z+}$ is an ammonium cation of formula (3)

$$[NR_4]^+ \qquad (3),$$

where
R in each case, independently of one another, is
H, OR', NR'$_2$, with the proviso that a maximum of one substituent R in formula (3) is OR' or NR'$_2$,
straight-chain or branched alkyl having 1-20 C atoms,
straight-chain or branched alkenyl having 2-20 C atoms and one or more double bonds, or straight-chain or branched alkynyl having 2-20 C atoms and one or more triple bonds, or
saturated, partially or fully unsaturated cycloalkyl having 3-7 C atoms, which is optionally substituted by alkyl groups having 1-6 C atoms,
where one or two R are optionally partially or fully substituted by halogens, or partially substituted by —OH, —OR', —CN, —NR'$_2$, —C(O)OH, —C(O)NR'$_2$, —SO$_2$NR'$_2$, —C(O)X, —SO$_2$OH, —SO$_2$X, —NO$_2$, —SR', —S(O)R', or —SO$_2$R', and
where one or two non-adjacent carbon atoms in R which are not in the α-position are optionally replaced by atoms and/or atom groups selected from —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N—, and —P(O)R'—,
R' is H, non-, partially or perfluorinated $C_1$- to $C_{18}$-alkyl, $C_3$- to $C_7$-cycloalkyl, nonsubstituted phenyl or substituted phenyl, and
X is halogen; or (b) $[Kt]^{z+}$ is a phosphonium cation of formula (4)

$$[PR^2_4]^+ \qquad (4),$$

where
$R^2$ in each case, independently of one another, is
H, OR' or NR'$_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds, or
saturated, partially or fully unsaturated cycloalkyl having 3-7 C atoms, which is optionally substituted by alkyl groups having 1-6 C atoms,
where one or two $R^2$ are optionally partially or fully substituted by halogens, or partially substituted by —OH, —OR', —CN, —NR'$_2$, —C(O)OH, —C(O)NR'$_2$, —SO$_2$NR'$_2$, —C(O)X, —SO$_2$OH, —SO$_2$X, —NO$_2$, —SR', —S(O)R', or —SO$_2$R', and
where one or two non-adjacent carbon atoms in $R^2$ which are not in the α-position are optionally replaced by atoms and/or atom groups selected from —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N—, and —P(O)R'—,
R' is H, non-, partially or perfluorinated $C_1$- to $C_{18}$-alkyl, $C_3$- to $C_7$-cycloalkyl, nonsubstituted phenyl or substituted phenyl, and
X is halogen; or (c) $[Kt]^{z+}$ is a uronium cation of formula (5)

$$[C(NR^3R^4)(OR^5)(NR^6R^7)]^+ \qquad (5),$$

where
$R^3$ to $R^7$ each, independently of one another, are
H, where H is excluded for $R^5$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds, or
saturated, partially or fully unsaturated cycloalkyl having 3-7 C atoms, which is optionally substituted by alkyl groups having 1-6 C atoms,
where one or more of the substituents $R^3$ to $R^7$ are optionally partially or fully substituted by halogens, or partially substituted by —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', or —NO$_2$, and where one or two non-adjacent carbon atoms in R$^3$ to R$^7$ which are not in the α-position are optionally replaced by atoms and/or atom groups selected from —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N—, and —P(O)R'—, R' is H, non-, partially or perfluorinated C$_1$- to C$_{18}$-alkyl, C$_3$- to C$_7$-cycloalkyl, nonsubstituted phenyl or substituted phenyl, and X is halogen; or (d) [Kt]$^{z+}$ is a thiouronium cation of formula (6)

[C(NR$^3$R$^4$)(SR$^5$)(NR$^6$R$^7$)]$^+$      (6), where
R$^3$ to R$^7$ each, independently of one another, are
H, where H is excluded for R$^5$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds, or
saturated, partially or fully unsaturated cycloalkyl having 3-7 C atoms, which is optionally substituted by alkyl groups having 1-6 C atoms,
where one or more of the substituents R$^3$ to R$^7$ are optionally partially or fully substituted by halogens, or partially substituted by —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', or —NO$_2$, and where one or two non-adjacent carbon atoms in R$^3$ to R$^7$ which are not in the α-position are optionally replaced by atoms and/or atom groups selected from —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N—, and —P(O)R'—, R' is H, non-, partially or perfluorinated C$_1$- to C$_{18}$-alkyl, C$_3$- to C$_7$-cycloalkyl, nonsubstituted phenyl, or substituted phenyl, and X is halogen; or (e) [Kt]$^{z+}$ is a guanidinium cation of formula (7)

[C(NR$^8$R$^9$)(NR$^{10}$R$^{11}$)(NR$^{12}$R$^{13}$)]$^+$      (7), where
R$^8$ to R$^{13}$ each, independently of one another, are
H, —CN, NR'$_2$, —OR',
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds, or
saturated, partially or fully unsaturated cycloalkyl having 3-7 C atoms, which is optionally substituted by alkyl groups having 1-6 C atoms,
where one or more of the substituents R$^8$ to R$^{13}$ are optionally partially or fully substituted by halogens, or partially substituted by —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', or —NO$_2$, and where one or two non-adjacent carbon atoms in R$^8$ to R$^{13}$ which are not in the α-position are optionally replaced by atoms and/or atom groups selected from —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N—, PR'$_2$=N—, and —P(O)R'—, R' is H, non-, partially or perfluorinated C$_1$- to C$_{18}$-alkyl, C$_3$- to C$_7$-cycloalkyl, nonsubstituted phenyl or substituted phenyl, and X is halogen; or (f) [Kt]$^{z+}$ is of formula (8)

[HetN]$^{z+}$      (8)

where
HetN$^{z+}$ is a heterocyclic cation selected from

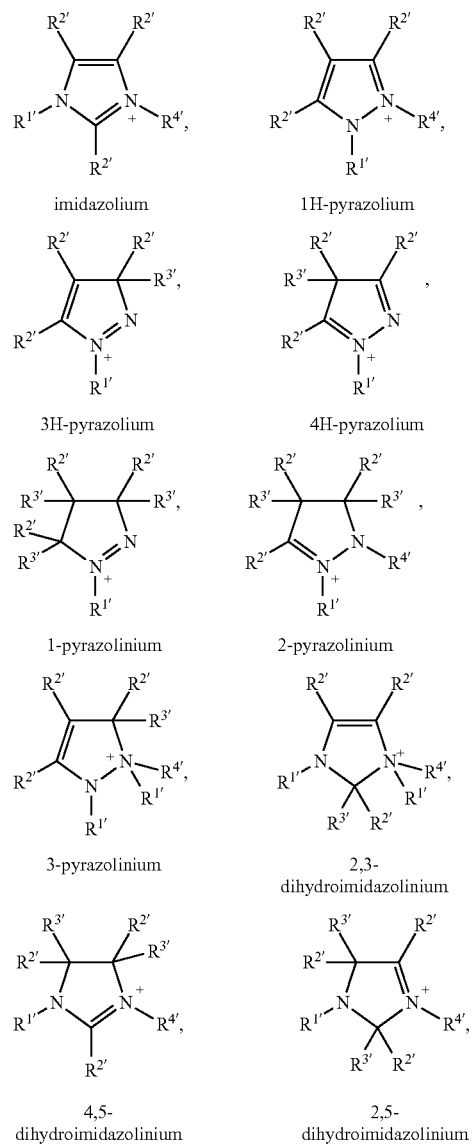

-continued

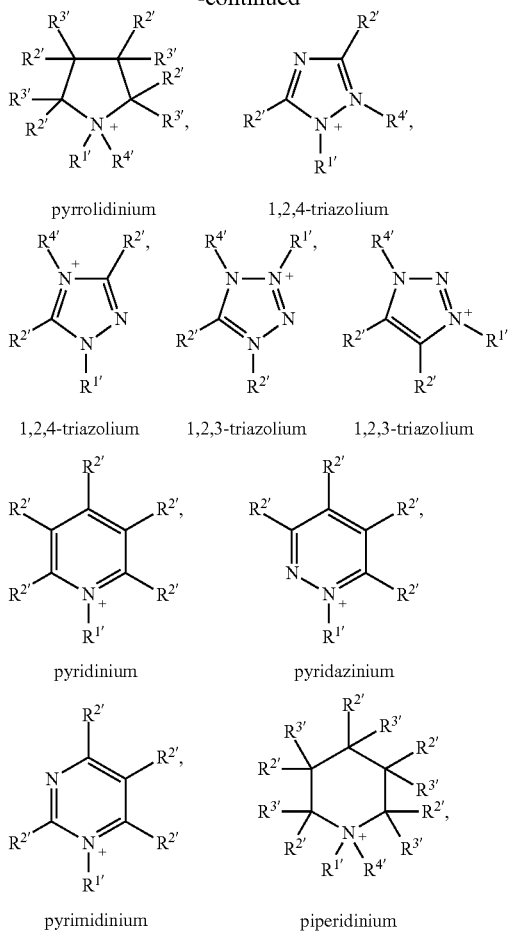

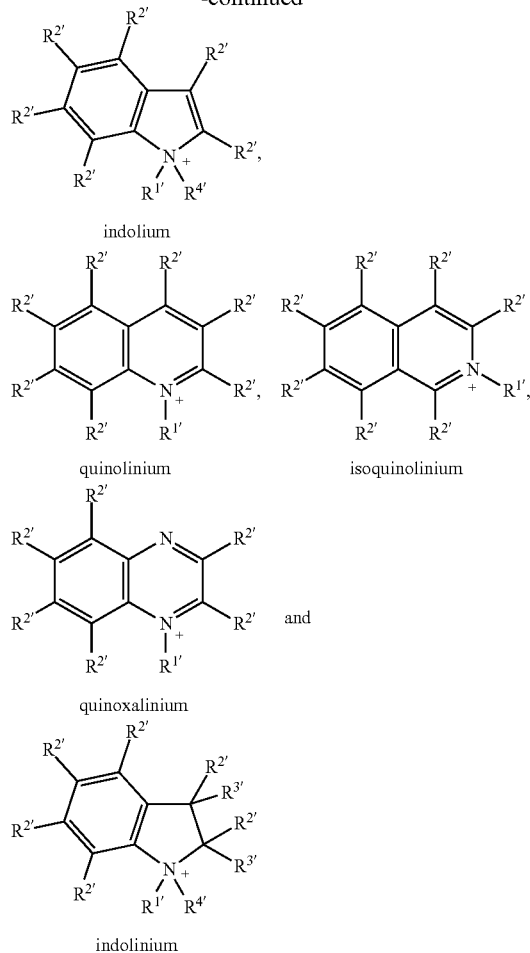

where
R$^{1'}$ to R$^{4'}$ each, independently of one another, are
H, F, Cl, Br, I, —CN, —OR', —NR'$_2$, —P(O)R'$_2$, —P(O)(OR')$_2$, —P(O)(NR'$_2$)$_2$, —C(O)R', —C(O)OR', —C(O)X, —C(O)NR'$_2$, —SO$_2$NR'$_2$, —SO$_2$OH, —SO$_2$X, —SR', —S(O)R', —SO$_2$R' or NO$_2$, with the proviso that, in this case, R$^{1'}$, R$^{3'}$, R$^{4'}$ are each H, straight-chain or branched alkyl having 1-20 C atoms, or straight-chain or branched alkenyl having 2-20 C atoms and one or more double bonds, straight-chain or branched alkyl having 1-20 C atoms, which is optionally fluorinated or perfluorinated, straight-chain or branched alkenyl having 2-20 C atoms and one or more double bonds, which is optionally fluorinated or perfluorinated, straight-chain or branched alkynyl having 2-20 C atoms and one or more triple bonds, which is optionally fluorinated or perfluorinated, saturated, partially or fully unsaturated cycloalkyl having 3-7 C atoms, which is optionally substituted by alkyl groups having 1-6 C atoms, and saturated, partially or fully unsaturated heteroaryl, heteroaryl-C$_1$-C$_6$-alkyl or aryl-C$_1$-C$_6$-alkyl, or substituents R$^{1'}$, R$^{2'}$, R$^{3'}$ and/or R$^{4'}$ together optionally form a ring system, where one or more substituents R$^{1'}$ to R$^{4'}$ are optionally partially or fully substituted by halogens, —OH, —OR', NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', or —NO$_2$, but where R$^{1'}$ and R$^{4'}$ cannot simultaneously be fully substituted by halogens, and where, in the substituents R$^{1'}$ to R$^{4'}$, one or two non-adjacent carbon atoms which are not bonded to the heteroatom are optionally replaced by atoms and/or atom groups selected from —O—, —S—, —S(O)—, —SO$_2$—, —SO$_2$O—, —C(O)—, —C(O)O—, —N$^+$R'$_2$—, —P(O)R'O—, —C(O)NR'—, —OP(O)R'O—, —P(O)(NR'$_2$)NR'—, —PR'$_2$=N—, and —P(O)R'—, R' is H, non-, partially or perfluorinated C$_1$- to C$_{18}$-alkyl, C$_3$- to C$_7$-cycloalkyl, nonsubstituted phenyl or substituted phenyl, and X is halogen.

6. A compound according to claim 2, wherein [Kt]$^{z+}$ is a metal cation or NO$^+$.

7. A process for the preparation of a compound of formula I according to claim 2 in which [Kt]$^{z+}$ is an alkalimetal cation and y=0, which is a compound of formula I-1,

[Me]$^+$[B(R$_f$)(CN)$_x$(OR*)$_{3-x}$]$^-$    I-1 where R$_f$, x and R* have the meanings indicated in claim 2, said process comprising:
reacting a compound of formula II

[Me]$^+$[B(R$_f$)(OR*)$_3$]$^-$    II in which
[Me]$^+$ is an alkalimetal cation, and
R$_f$ is a straight-chain or branched perfluoroalkyl group having 1 to 4 C atoms, C$_6$F$_5$, C$_6$H$_5$, partially fluorinated phenyl, or phenyl which is monosubstituted or disubstituted by perfluoroalkyl groups having 1 to 4 C atoms,
with trialkylsilylcyanide in which the alkyl groups independently are straight-chain or branched alkyl groups having 1 to 4 C atoms.

8. A process according to claim 7, where the reaction temperature is between 10° C. and 200° C.

9. A process according to claim 7, wherein (a) the reaction temperature is between 10° C. and 70° C., stoichiometric amounts of the compound of formula II are used, and compounds of formula I-1 in which x is 1 are obtained; or (b) the reaction temperature is between 10° C. and 200° C., more than one equivalent of the compound of formula II is used, and compounds of formula I-1 in which x is 2 are obtained.

10. A process for the preparation of a compound of formula I according to claim 2 in which [Kt]$^{z+}$ is an alkalimetal cation and y=1 and x=1 which denotes a compound of formula I-2,

[Me]$^+$[B(R$_f$)(CN)(OR*)(F)]$^-$    I-2 and R$_f$ and R* have the meanings indicated in claim 2, said process comprising:
reacting a compound of formula III

[Me]$^+$[B(R$_f$)(OR*)F$_2$]$^-$    III in which
[Me]$^+$ is an alkalimetal cation, and
R$_f$ is a straight-chain or branched perfluoroalkyl group having 1 to 4 C atoms, C$_6$F$_5$, C$_6$H$_5$, partially fluorinated phenyl, or phenyl which is monosubstituted or disubstituted by perfluoroalkyl groups having 1 to 4 C atoms, and
R* is a straight-chain or branched alkyl group having 1 to 4 C atoms
with trialkylsilylcyanide in which the alkyl groups independently are straight-chain or branched alkyl groups having 1 to 4 C atoms.

11. A process for the preparation of a compound of formula I according to claim 2, in a salt-exchange reaction, said process comprising:
reacting an alkalimetal salt of formula I-1 or of formula I-2

[Me]$^+$[B(R$_f$)(CN)$_x$(OR*)$_{3-x}$]$^-$    I-1

[Me]$^+$[B(R$_f$)(CN)(OR*)(F)]$^-$    I-2 in which
Me is an alkalimetal cation or H$^+$, and
Rf, x, and R* have the meanings indicated in claim 2,
with a compound of formula V KtA    V, in which
Kt is an organic cation or a metal cation other than the alkalimetal cation of the compound of formula I-1 or formula I-2, and
A denotes F$^-$, Cl$^-$, Br$^-$, I$^-$, OH$^-$, [HF$_2$]$^-$, [CN]$^-$, [SCN]$^-$, [R$_1$COO]$^-$, [R$_1$SO$_3$]$^-$, [R$_2$COO]$^-$, [R$_2$SO$_3$]$^-$, [R$_1$OSO$_3$]$^-$, [SiF$_6$]$^{2-}$, [BF$_4$]$^-$, [SO$_4$]$^{2-}$, [HSO$_4$]$^{1-}$, [NO$_3$]$^-$, [(R$_2$)$_2$P(O)O]$^-$, [R$_2$P(O)O$_2$]$^{2-}$, tosylate, benzoate, oxalate, succinate, suberate, ascorbate, sorbate, tartrate, citrate, malate, malonate, the malonate optionally substituted with straight-chain or branched alkyl groups having 1 to 4 C atoms or [CO$_3$]$^{2-}$,
in which R$_1$ is each case, independently of another, a straight-chain or branched alkyl group having 1 to 12 C atoms, and
R$_2$ is each independently of one another a straight-chain or branched perfluorinated alkyl group having 1 to 12 C atoms, and
where electroneutrality should be taken into consideration in the formula of the salt KtA.

12. An electrolyte formulation comprising at least one compound containing a borate anion of formula Ia according to claim 1.

13. The electrolyte formulation according to claim 12 comprising the borate anion of formula Ia in molar concentrations from 0.1 to 3 M.

14. An electrochemical and/or optoelectronic device comprising an electrolyte formulation according to claim 12.

15. A device according to claim 14 which is a photovoltaic cell, a light emitting device, an electrochromic or photoelectrochromic device, an electrochemical sensor and/or biosensor.

\* \* \* \* \*